(12) United States Patent
Rubin et al.

(10) Patent No.: US 9,737,205 B2
(45) Date of Patent: Aug. 22, 2017

(54) METHOD AND SYSTEM FOR EVALUATING PROGRESSION OF AGE-RELATED MACULAR DEGENERATION

(71) Applicant: The Board of Trustees of the Leland Stanford Junior University, Stanford, CA (US)

(72) Inventors: Daniel L. Rubin, Stanford, CA (US); Luis de Sisternes Garcia, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 2 days.

(21) Appl. No.: 14/908,519

(22) PCT Filed: Jul. 30, 2014

(86) PCT No.: PCT/US2014/048886
§ 371 (c)(1),
(2) Date: Jan. 28, 2016

(87) PCT Pub. No.: WO2015/017536
PCT Pub. Date: Feb. 5, 2015

(65) Prior Publication Data
US 2016/0174830 A1 Jun. 23, 2016

Related U.S. Application Data

(60) Provisional application No. 61/860,544, filed on Jul. 31, 2013.

(51) Int. Cl.
*A61B 3/14* (2006.01)
*A61B 3/00* (2006.01)
(Continued)

(52) U.S. Cl.
CPC ............ *A61B 3/0025* (2013.01); *A61B 3/102* (2013.01); *A61B 3/1225* (2013.01);
(Continued)

(58) Field of Classification Search
CPC ...... A61B 3/0025; A61B 3/102; A61B 3/1225
(Continued)

(56) References Cited

U.S. PATENT DOCUMENTS

2008/0309881 A1 12/2008 Huang et al.
2012/0107315 A1 5/2012 Behrens et al.
(Continued)

FOREIGN PATENT DOCUMENTS

JP 2012-071043 A 4/2012

OTHER PUBLICATIONS

Barker, J., et al., "Automated Classification of Brain Tumor Type in Whole-Slide Digital Pathology Images Using Local Representative Tiles," Medical Image Analysis (2015), doi: 10.1016/j.media.2015.12.002, 26 pp.
(Continued)

*Primary Examiner* — Jack Dinh
(74) *Attorney, Agent, or Firm* — Brian E. Davy; Bozicevic, Field & Francis LLP

(57) ABSTRACT

Disclosed is a method for analyzing retinal image data obtained using spectral-domain optical coherence tomography (SD-OCT). The image data comprise a cross-section of the retina and an en face image of the retina of a subject having AMD (age-related macular degeneration). The image data are processed to obtain an accurate structure showing locations, shape, size, and other data on drusen (deposits under the retina). This structural information is processed to extract quantitative drusen features that are indicative of a risk of progression of AMD from the dry form to the wet form of the disease in a given subject and defined time
(Continued)

period, including short time intervals (one year or less). Relevant drusen features used include number, en face area and volume of drusen detected; shape of drusen detected; density of drusen; and reflectivity of drusen. The method uses the extracted drusen features in combination with clinical data and measurement of the changes of the quantitative image features over time to derive a risk score for whether or not the subject will progress from dry AMD to wet AMD in a defined time period.

19 Claims, 18 Drawing Sheets

(51) Int. Cl.
  A61B 3/10 (2006.01)
  G06T 7/00 (2017.01)
  A61B 3/12 (2006.01)
(52) U.S. Cl.
  CPC .. *G06T 7/0012* (2013.01); *G06T 2207/10101* (2013.01); *G06T 2207/30041* (2013.01)
(58) Field of Classification Search
  USPC .................................................. 351/206, 246
  See application file for complete search history.

(56) References Cited

U.S. PATENT DOCUMENTS

2012/0127427 A1  5/2012  Guo et al.
2012/0251452 A1  10/2012  Verdooner

OTHER PUBLICATIONS

Bozkurt, S., et al., "Automated abstraction of imaging observations with their characteristics from mammography reports," J Am Med Inform Assoc 2015;22:e81-e92. doi:10.1136/amiajnl-2014-003009, Research and Applications (Abstract).

Burnside, E., et al., "A Bayesian Network for Mammography," AMIA, Inc. (2000), pp. 106-110.

Chen, Q., et al., "Semi-automatic geographic atrophy segmentation for SD-OCT images," Biomedical Optics Express (2013) 4(12):2729-2750.

Chen, Q., et al., "Automated Drusen Segmentation and Quantification in SD-OCT Images," Med Imag Anal. (2013) 17(8):1058-1072.

Chen, Q., et al., "A False Color Fusion Strategy for Drusen and GA Visualization in OCT Images," Retina (2014) 34(12):2346-2358.

De Sisternes, L., et al., "Quantitative SD-OCT Imaging Biomarkers as Indicators of Age-Related Macular Degeneration Progression," Invest Ophthalmol Vis Sci. (2014) 55:7093-7103.

De Sisternes, L., et al., "Visual Prognosis of Eyes Recovering from Macular Hole Surgery Through Automated Quantitative Analysis of Spectral-Domain Optical Coherence Tomography (SD-OCT) Scans," Invest Ophthalmol Vis Sci.(2015) 56:4631-4643.

Ertosun, M., et al., "Automated Grading of Gliomas using Deep Learning in Digital Pathology Images: A modular approach with ensemble of convolutional neural networks," AMIA Symposium Proceedings (2015) 1899-1908.

Kahn, C., Jr., et al., "Informatics in Radiology: An Information Model of the DICOM Standard," RadioGraphics (2011) 31:295-304.

Kurtz, C., et al., "On combining image-based and ontologial semantic dissimilarities for medical image retrieval applications," Med Image Anal. (2014) 18:(7):1082-1100.

Levy, M., et al., "Current and future trends in imaging informatics for oncology," Cancer J. (2011) 17(4):203-210.

Mendelson, D. and Rubin, D., "Imaging Informatics: Essential Tools for the Delivery of Imaging Services," Acad Radiol. (2013) 20(10):1195-1212.

Niu, S., et al., "Automated geographic atrophy segmentation for SD-OCT images using region-based C-V model via local similarity factor," Biomedical Optics Express (2016) 7(2):581-600.

Weizman, L., et al., "Semiautomatic segmentation and follow-up of multicomponent low-grade tumors in longitudinal brain MRI studies," Med. Phys. (2014) 41(5):052303-1-14.

Xu, J., et al., "A Comprehensive Descriptor of Shape: Method and Application to Content-Based Retrieval of Similar Appearing Lesions in Medical Images," J Digit Imaging (2012) 25:121-128.

Xu, J., et al., "Quantifying the margin sharpness of lesions on radiological images for content-based image retrieval," Med. Phys. (2012) 39(9):5405-5418.

METHOD AND SYSTEM FOR EVALUATING PROGRESSION OF AGE-RELATED MACULAR DEGENERATION

CROSS-REFERENCE TO RELATED APPLICATIONS

This application claims priority from U.S. Provisional Patent Application No. 61/860,544 filed Jul. 31, 2013, which is hereby incorporated by reference, and is a national phase filing of PCT Patent Application No. PCT/US2014/48886 filed on Jul. 30, 2014, the disclosure of which is hereby incorporated by reference in its entirety.

STATEMENT OF GOVERNMENTAL SUPPORT

This invention was made with Government support under Contract No. U01-CA-142555 awarded by the National Institutes of Health. The Government has certain rights in the invention.

REFERENCE TO SEQUENCE LISTING, COMPUTER PROGRAM, OR COMPACT DISK

None

BACKGROUND OF THE INVENTION

Field of the Invention

This invention relates to methods and systems for studying age-related macular degeneration and further to methods for image analysis in an optical-coherence image.

Background

Presented below is background information on certain aspects of the present invention as they may relate to technical features referred to in the detailed description, but not necessarily described in detail. The discussion below should not be construed as an admission as to the relevance of the information to the claimed invention or the prior art effect of the material described.

Age-related macular degeneration (AMD) is the leading cause of irreversible severe vision loss in the developed world in individuals over the age of 65. AMD can manifest in its non-exudative form or in its more advanced exudative form, also known as dry AMD and wet AMD respectively. Dry AMD usually manifests without any symptoms of vision loss and always precedes the development of the more severe wet form. Early detection and prompt intervention in progressing cases of AMD have been shown to increase visual outcome, so it is crucial to identify signs of wet development at the earliest stage as possible. Once severe AMD fully develops, most treatments have suboptimal visual outcomes; thus new approaches to identify patients at high risk for developing severe AMD to enable early detection of disease progression and protective intervention are critical.

Patients presenting with dry AMD can suddenly progress to wet AMD without any previous noticeable visual changes, and eye care professionals have currently no reliable method to tell if and when the dry form will turn into the more severe wet form. Considering the low incidence of patients progressing to the wet form (only about 10% of cases actually progress) severe AMD is usually detected once visual changes are irreversible. Successful and reliable prediction of AMD progression in the near future is a challenging problem that is unsolved to date.

Development of technology to accurately identify if a patient will develop wet AMD in the near term or in the longer term would be a major advance in AMD management since such technology would allow following patients according to how prone they are to progression to web AMD, permitting more frequent screening evaluation and potential earlier treatment of those patients or subjects with higher chances for AMD progression. This technology may also provide better biomarkers of AMD, enabling clinical drug trials for the treatment of dry AMD to prevent progression, by helping to evaluate the chances that a patient will develop AMD before and after receiving treatment.

Drusen are extracellular deposits that accumulate between the retinal pigment epithelium (RPE) and the inner collagenous layer of Bush's membrane, and they commonly appear with aging. Non-neovascular (dry) AMD is normally identified by a greater accumulation of drusen. Evaluation of color fundus photographs (CFPs) represents the current clinical practice standard for drusen assessment in dry AMD. It has been found that there is positive correlation in the number, size and extent of drusen observed in CFPs with risk of wet AMD progression in more than two years. In current clinical practice, patients presenting drusen in CFPs are diagnosed with dry AMD, and are later classified in three different progression risk categories (early, intermediate and advanced) according to drusen number, area and maximum size. These characteristics of drusen are usually estimated by visual inspection of CFPs with comparison to a set of standardized circles drawn either manually or semi-automatically. This classification is limited because it is very coarse (it can only identify a subgroup of patients with a maximum risk of progression or 8.8% over two years), and even patients classified with early dry AMD can suddenly turn into the wet form. Drusen can sometimes also be hard to identify in CFPs, and manual measurements are prone to human-induced errors and reader variability. Current assessment methods also do not take advantage of drusen volumetric properties (there is no depth resolution in CFPs) or the information obtained by quantitatively evaluating the changes drusen observed as AMD progresses over time. Current experimental AMD progression predictive methods include a combination of the afore-mentioned drusen classification in CFPs combined with genetic, demographic, and environmental factors such as smoking or diet. While these methods show promising results, they still not exploit a variety of quantitative features of drusen such as volumetric properties which may have a role in AMD progression.

Optical coherence tomography (OCT) is potentially highly valuable in providing imaging data useful for predicting AMD progress. OCT is an-vivo imaging method capable of resolving cross-sectional retinal substructures. In recent years, it has become a key diagnostic technology in the areas of retinal diseases and glaucoma, as well as among a diverse set of medical and surgical specialties, including gastroenterology, dermatology, cardiology, and oncology, among others. The technique was commercialized by Carl Zeiss Meditec, Inc. for inner retina imaging and is now considered superior to the current standard of care for the evaluation of a number of conditions. The more recently introduced Spectral Domain OCT (SD-OCT) allows very fast scanning (more than 20 000 axial scans per second) over a retinal area, with depth resolutions smaller than 5 µm, which makes possible three-dimensional visualization of high-resolution retinal substructure while minimizing artifacts due to patient movement or ocular contractions. SD-OCT is suitable for visualizing and quantifying the changes seen at different stages of AMD, because the RPE, the site of many of those pathological changes, is normally well visualized in OCT. Drusen normally appear in SD-OCT images as "bumps" in an otherwise smoothly curved RPE layer. SD-OCT enables the accurate identification of drusen and its depth differentiation allows quantification of their volumetric and reflective properties.

Previous studies indicate that there is a degenerative retinal process associated with the height of drusen observed in SD-OCT imaging. However, many other drusen characteristics have not been previously quantified via SD-OCT.

BRIEF SUMMARY OF THE INVENTION

The present invention relates to and includes a method and a system in which AMD progression can be predicted by extracting and computationally analyzing quantitative imaging features from SD-OCT images of the retina. The invention further includes an imaging processing method that provides an automated method/system to characterize quantitative features of drusen in SD-OCT images. The present methods also comprise a method for predicting AMD progression, including processing form the dry form of AMD to the wet form. Using the features identified here as relevant, the present method generates classifications of the features. One may use the described classifier(s) to identify patients which are prone to develop wet AMD within a given time frame, a challenging problem that is unsolved to date. Images in a large database of SD-OCT scans (2146 scans from 350 eyes of 261 patients) obtained from patients presenting at different stages of AMD development were automatically segmented to identify the presence and boundary of drusen. A set of quantitative imaging features was then obtained from the segmented drusen to characterize quantitatively the AMD disease process. These features were then evaluated using statistical methods to determine those which are most informative in predicting the future development of wet AMD from a dry stage (i.e. progression of AMD) in a retrospective study. With the use of machine learning methods the present classifier that predicts those patients in whom AMD will progress within a given time interval has been derived, based on analysis of the extracted quantitative imaging features and pertinent clinical data. The classifier was evaluated in a retrospective analysis of the AMD patients (some of whom had AMD and some of whom did not progress) to assess the accuracy of our invention to predict AMD progression.

The present invention further comprises analysis of drusen features derived from SD-OCT that are useful as disease biomarkers. Drusen segmentation refers to the identification of drusen and their boundaries so as to distinguish them from related tissue that appears in the SD-OCT images (considered as "background" for segmentation purposes). Drusen segmentations, as used herein, are the drusen as defined by the boundaries obtained after the present imaging processing. Other, different, drusen segmentation algorithms exist in the literature and are oriented for the extraction of quantitative features of drusen. However, while drusen segmentation methods exists in previous literature, the present invention provides drusen imaging methods that can accurately identifies patients likely to develop wet AMD in a quantitative, fully automated, and reproducible manner.

In certain aspects, the present invention comprises a method for analyzing optical coherence tomography ("OCT") images of a retina, comprising the steps of: (a) obtaining a subject's demographic data, including age (in months) gender (0 or 1), presence of age-related macular degeneration ("AMD") (0 for non-present, 1 for present), and further obtaining OCT images of the subject's retina; (b) processing OCT images of step (a) to define an inner retinal pigment epithelium boundary and an outer retinal pigment epithelium boundary, and thereby identifying a region for examining said image for drusen using computerized (automatic) imaging and calculating steps; (c) identifying drusen using boundaries defined in step (b) and further characterizing identified drusen by quantitative values for at least one of: (i) drusen slope expressed as height versus a length in an en face area; (ii) drusen reflectivity expressed as pixel intensity; (iii) drusen height (iv) drusen area, (v) drusen volume, and (vi) drusen number, wherein measured values of the various listed features are also measured at separate time points, and a difference in measurements between time points is calculated (i.e. a second measurement of the same feature on the same eye a month, multiple months or years later); and (d) using quantitative values obtained in step (c) and demographic data from step (a) to obtain a score wherein increases in its quantitative value indicates an increased likelihood of progressing from dry AMD to wet AMD. The term "logic means" as used herein refers to a computing device that can be or has been programmed to input data and carry out mathematical calculations on such data, resulting in a readable output. Similarly, "storage means" refers to various data storage devices, e.g. hard drives, flash drive, computer ram and rom, etc.

In certain embodiments, the present invention further comprises a method as described above herein the quantitative values measured and used in the score are all of (iii) through (vii), inclusive.

In certain embodiments, the present invention further comprises the step of using OCT images in step (a) comprises using SD-OCT ("spectral domain" OCT or "fourier domain" OCT)\as the OCT images analyzed.

In certain embodiments, the present invention further comprises the use of demographic data that includes at least one of: exceeding or not an age of 60 years (increased risk); (b) a previous diagnosis of dry AMD (increased risk compared to no AMD); and (c) a genetic predisposition to AMD (increased risk).

In certain embodiments, the present invention further comprises the step of processing said OCT images so as to improve retinal pigment epithelium ("RPE") boundary determination by including determination of one or more of the following retina layer boundaries: inner limiting membrane (ILM), inner retinal nerve fiber layer boundary (iRNFL), outer retinal nerve fiber layer boundary (oRNFL), outer boundary of the inner plexiform layer (IPL), outer boundary of the inner nuclear layer (INL), outer boundary of the outer plexiform layer (OPL), innerboundary of the inner segment/outer segment junction (IS), and outer boundary of the inner segment/outer segment junction (OS), in addition to inner retinal pigment epithelium boundary (iRPE), and outer retinal pigment epithelium boundary (oRPE). In some embodiments, the present methods include the use of some subset, or all of the foregoing layer determinations.

In certain embodiments, the present invention further comprises calculation of particular curvature, reflectivity and topology to identify, segment and characterize drusen.

In certain embodiments, the present invention further comprises a method as described above that further includes measuring maximum drusen height, wherein in increased in drusen height indicates an increased likelihood of progression to wet AMD.

In certain embodiments, the present invention further comprises a method as described above further comprising measuring standard deviation of pixel intensity relating to drusen reflectivity.

In certain embodiments, the present invention further comprises further comprising the step of comparing previously measured values from other patients to those measured in step (c), wherein increased values in measured values in step (c) compared to previously measured values indicate in increased likelihood of progression from dry AMD to wet AMD.

In certain embodiments, the present invention further comprises a method for analyzing optical coherence tomography ("OCT") images of a retina, comprising the steps of: (a) obtaining a subject's demographic data, including age, gender, presence of age-related macular degeneration ("AMD"), and further obtaining OCT images of the subject's retina; (b) processing OCT images of step (a) to define segmentations of three dimensional retinal layers, including an inner boundary and an outer boundary of retinal pigment epithelium (RPE); (c) identifying drusen segmentations using boundaries obtained in step (b); (d) using drusen segmentations calculated in step (c) to determine a plurality of three-dimensional drusen features having individual numerical values; and (e) using (i) the individual numerical values obtained in step (d); (ii) historical numerical values corresponding to values measured in step (d); and (iii) subject demographic data in step (a) to obtain an AMD score representing a likelihood of progression of AMD.

In certain embodiments, the present invention further comprises a method for assessing risk for progression in Age-Related Macular Degeneration ("AMD"), comprising the steps of: (a) obtaining subject demographic data and OCT images of said retina; (b) processing said OCT images to define segmentations of three dimensional retinal layers, including an inner boundary and an outer boundary of retinal pigment epithelium (RPE); (c) identifying drusen segmentations using boundaries obtained in step (b); (d) using drusen segmentations calculated in step (c) to determine a plurality of three dimensional drusen features having individual a numerical values comprising (i) number of drusen identified, (ii) extent of retinal area affected by drusen, (iii) mean area per drusen detected, (iv) mean volume of drusen detected, (v) shape of drusen detected, (vi) density of drusen, and (vii) reflectivity of drusen; and (e) using (i) the individual numerical values obtained in step (d); (ii) historical numerical values corresponding to values measured in step (d); and (iii) subject demographic data in step (a) to assess a risk of progression of AMD, wherein higher values of values in (i) through (vii) indicate a higher risk of progression.

In certain embodiments, the present invention further comprises the use of an automated system wherein an OCT device, which contains a programmable computer, comprises instructions for carrying out the image processing and risk calculations described above by preprogrammed control. Thus, the present methods may be carried out by an OCT optical setup operative connected to a computer configured to carry out and store retinal images derived according to one of the present methods.

The present invention includes use of features as listed in Table 1, features $F_1$-$F_2$ being demographic; $F_3$-$F_{14}$ being quantitative measurements of drusen obtained from OCT scans that have been processed according to the described image processing steps; and $F_{15}$-$F_{26}$ are calculated values based on $F_3$-$F_{14}$, providing values of changes of those values over time. The exemplified calculations of a slope of linear fit and the parameters of mm. $mm^2$ and monthly measurements are illustrative and not intended to be limiting.

BRIEF DESCRIPTION OF THE DRAWINGS

FIG. 1 illustrates the results of SD-OCT scans that may be produced by commercially available equipment, at box 102, which leads as shown by arrow 104, to step (1) automated drusen segmentation. Other available patient knowledge are demographics 106, which is used as indicated by arrow 106 to for predictive model design; and known data of conversion from dry AMD to wet AMD, as shown in 108, which leads, as shown by arrow 110 is used to test the accuracy of the predictions of conversion from dry AMD to wet AMD. Key elements and processing pipeline are shown as follows: (1) Automated drusen segmentation. (2) Automated drusen feature extraction and quantification. (3) Predictive model design given patients in training set. (4) Predictive model testing for patients in test set.

In FIG. 4, the RPE inner and outer boundaries are identified and processed by data algorithms that flatten the boundaries, carry out inner RPE and outer RPE using spline fitting, and identify differences between the segmentation and fitting results. The result of this process is a drusen refinement that is used for feature analysis.

FIG. 7A shows the number of visits collected as a function of elapsed time to the next clinical visit of the same eye (follow-up time); FIG. 7B shows the percentage of observations as a function of the computed prediction score, divided in two groups: those in which no progression event was detected at a follow-up visit of the same eye and those which a progression event was detected at a follow-up visit. FIG. 7C is an ROC (receiver operating characteristic) curve that shows the performance of the proposed present binary classifier system as its discrimination threshold is varied when computing risks scores at follow-up time for each observation.

FIG. 8A is a histogram showing the number of observations as a function of risk scores for progressing from dry AMD to wet AMD, divided in two groups: those in which no progression event was detected at 12 months since clinical visit and those which a progression event was detected at 12 months since clinical visit. FIG. 8B is histogram comparing progressing (from dry to wet) observations with non-progressing (as in 8A) based on percentage of observations per class. FIG. 8C is a representation of the ROC curve that shows the performance of the proposed binary classifier system testing for progression events within 12 months of a clinical visit.

FIG. 9A shows the overall survival for all eyes considered in the evaluation; FIG. 9B shows a comparison of survival between those eyes predicted to progress and those not predicted to progress. As can be seen, those predicted to progress had a significantly higher actual rate of progression.

DETAILED DESCRIPTION OF THE INVENTION

Overview

Figure 1:
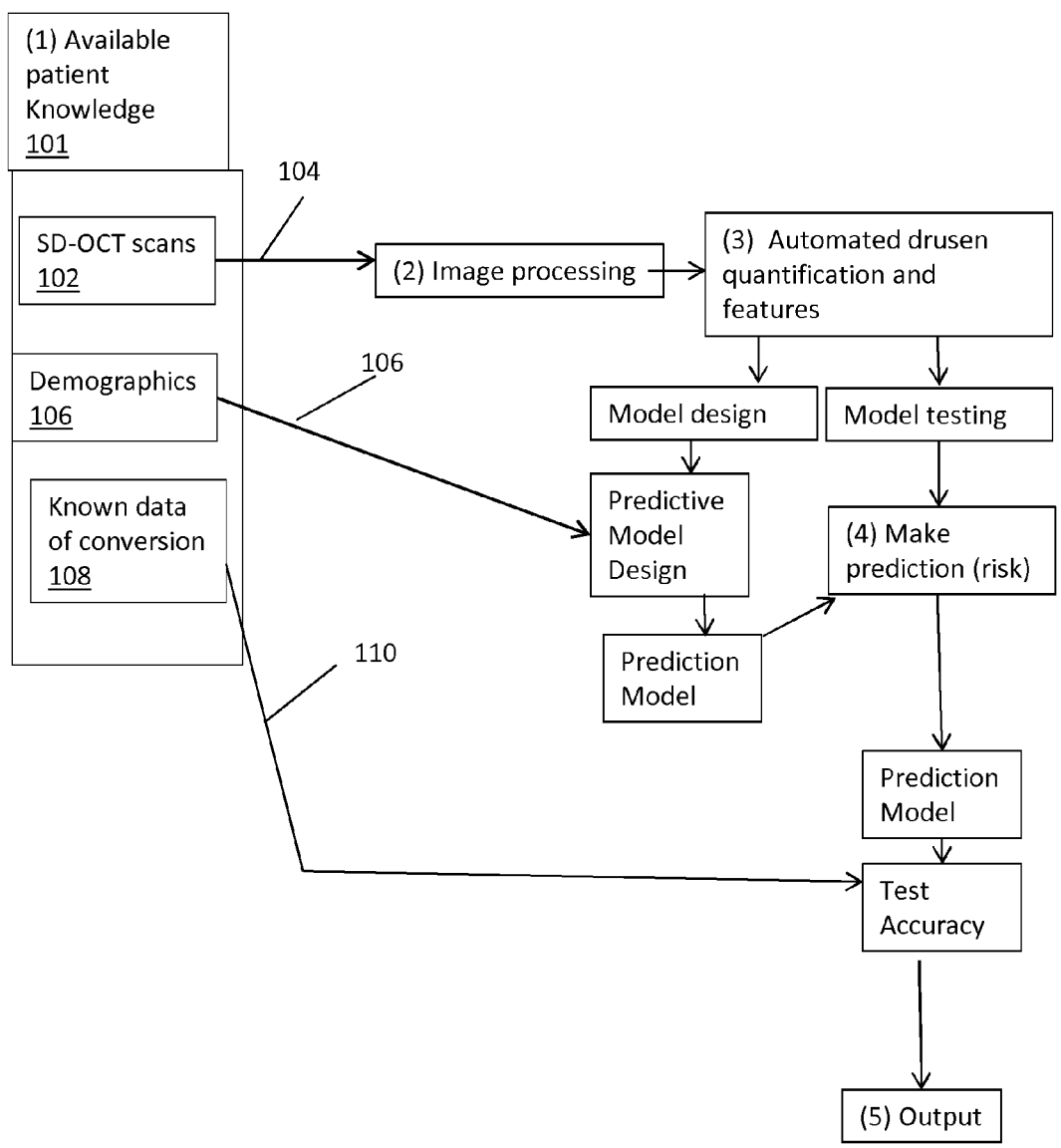
FIG. 1 is a schematic representation of the present method, showing creation and use of the present image analysis and patient (subject) data analysis. It shows the key steps, starting with use of available patient knowledge, including SD-OCT scans prior to wet conversion. In summary, the flow chart of the present invention proceeds from input of patient data, including various OCT scans taken from the patient (step 1), proceeds to image processing (step 2) which includes three-dimensional (3-D) retinal layer segmentation to localize drusen image signals and 3-D drusen segmentation (isolation), and then, using the patient data and features identified in the drusen segmentation, the calculation of a risk score of likelihood of conversion from dry AMD to wet AMD, shown at (4). Finally, the process proceeds to an output (5) that may be communicated to a physician and or a patient, and comprise a numerical score based on present values, and may be stored in a computer medium, and further tracked over time with later scores. In particular.

There is provided here a method and a system in which AMD progression can be predicted by extracting and computationally analyzing quantitative imaging features from SD-OCT images of the retina as well as considering relevant patient demographics and clinical history. The invention comprises an automated method/system to characterize quantitative features of drusen in SD-OCT images that appear promising to predict AMD progression. Using the features relevant in the prediction, the invention classifies which patients are prone to develop wet AMD within a given time frame, a challenging problem that is unsolved to date, particularly for predicting progression within short time frames (e.g., less than one year). The key elements of the present method and processing pipeline are shown in FIG. 1. Three-dimensional images are obtained though SD-OCT imaging and they are automatically processed to identify the presence and boundary of drusen. A set of quantitative imaging features is then obtained from the segmented drusen to characterize quantitatively the AMD disease process. These features are then evaluated together with demographic and known previous patient clinical data using statistical and machine learning methods to predict those patients in whom AMD will progress within a given time interval, including short time intervals of less than one year. The present classifier was evaluated in a retrospective analysis of the AMD patients (2146 scans from 350 eyes of 261 patients taken over 5 years, some of whom progressed to advanced AMD during study time and some of whom did not progress) to demonstrate effectiveness of the present invention and show its accuracy to predict AMD progression. Following is a description of each component of the methods of the invention.

(1) Input: Patient Data

At each patient clinical visit, one collects the patient's age, gender, relevant diagnosis history and SD-OCT images, which will be used as input in our prediction method.

(2) Image Processing

A method that is part of the invention automatically segments the three-dimensional location of the retinal boundaries in the collected SD-OCT images (3D-retina layer segmentation). Using the inner and outer boundaries of the segmentation results for the retinal pigment epithelium (RPE) layer, the method automatically identifies and segments drusen in three-dimensions as observed in the SD-OCT images. The original scans and segmented data are stored along with previous data collected and processed at a patient's previous clinical visits. A short description of the automated segmentation methods involved in this process follows.

3-D Retina Layer Segmentation

An automated method is used for the segmentation of 10 retinal boundaries in SD-OCT scans. As is known, "layer segmentation" refers to processing OCT images so as to define different layers that can be seen in cross section. The present method determines up to 10 segments, as described below.

Figure 2A:
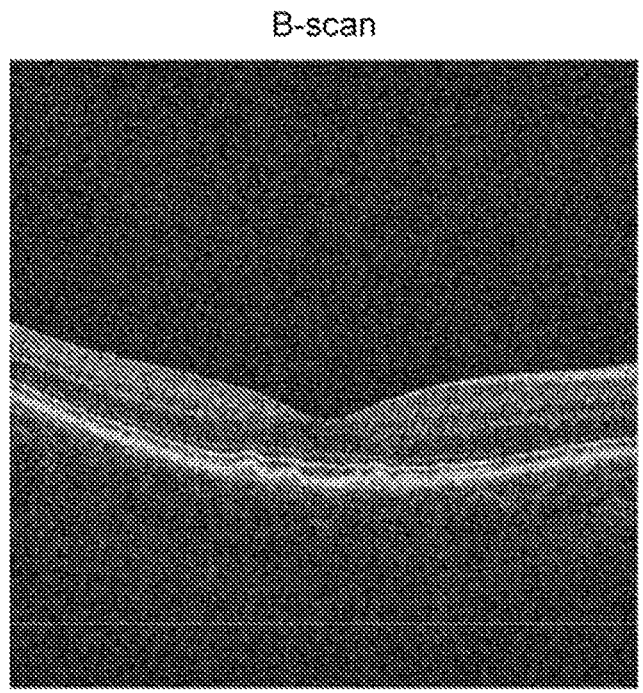
FIGS. 2A and 2B are a pair of B scans of OCT (i.e. two-dimensional cross-sectional view) showing an image as obtained (FIG. 2A) and as defined by boundary identification (FIG. 2B). The segmentation in FIG. 2B is marked on the image by lines (labeled in FIG. 2B), where the 10 segmented boundaries are shown, from top to bottom: inner limiting membrane (ILM), inner retinal nerve fiber layer boundary (iRNFL), outer retinal nerve fiber layer boundary (oRNFL), outer boundary of the inner plexiform layer (IPL), outer boundary of the inner nuclear layer (INL), outer boundary of the outer plexiform layer (OPL), inner boundary of the inner segment/outer segment junction (IS), outer boundary of the inner segment/outer segment junction (OS), inner retinal pigment epithelium boundary (iRPE), and outer retinal pigment epithelium boundary (oRPE).

Accuracy of the method for scans acquired in clinical practice from patients presenting healthy eyes and eyes presenting AMD at several disease stages was verified a priori by comparison to manual markings made by two different readers, yielding differences lower than those observed between the readers and a higher visual accuracy for our proposed automated method (publication of results pending). The method outlines the following 10 boundaries: Inner Limiting Membrane (ILM), inner Retinal Nerve Fiber Layer boundary (iRNFL), outer Retinal Nerve Fiber Layer boundary (oRNFL), outer boundary of the Inner Plexiform Layer (IPL), outer boundary of the Inner Nuclear Layer (INL), outer boundary of the Outer Plexiform Layer (OPL), inner boundary of the Inner Segment/Outer Segment Junction (IS), outer boundary of the Inner Segment/Outer Segment Junction (OS), inner Retinal Pigment Epithelium boundary (iRPE), and outer Retinal Pigment Epithelium boundary (oRPE). An example of the location of the ten segmented boundaries within the retina is given in FIG. 2A-C: (a) shows an example original SD-OCT B-scan as acquired with a CirrusOCT instrument (Carl Zeiss Meditec, Inc., Dublin, Calif.)—a clinical instrument used very commonly in many Ophthalmology practices, (b) shows the segmented B-scan, where each boundary location is indicated within the B-scan, with labels as indicated in the legend, (c) shows a 3D representation of the segmented boundaries within the SD-OCT cube (depth differences between the layers are exaggerated for displaying purposes). For most cases, as the one in the example shown in FIG. 2A-2C, the ILM and iRNFL boundaries remain in the same location. The differentiation between ILM and iRNFL was defined to correctly segment those cases presenting vitreous detachment.

Figure 2B:
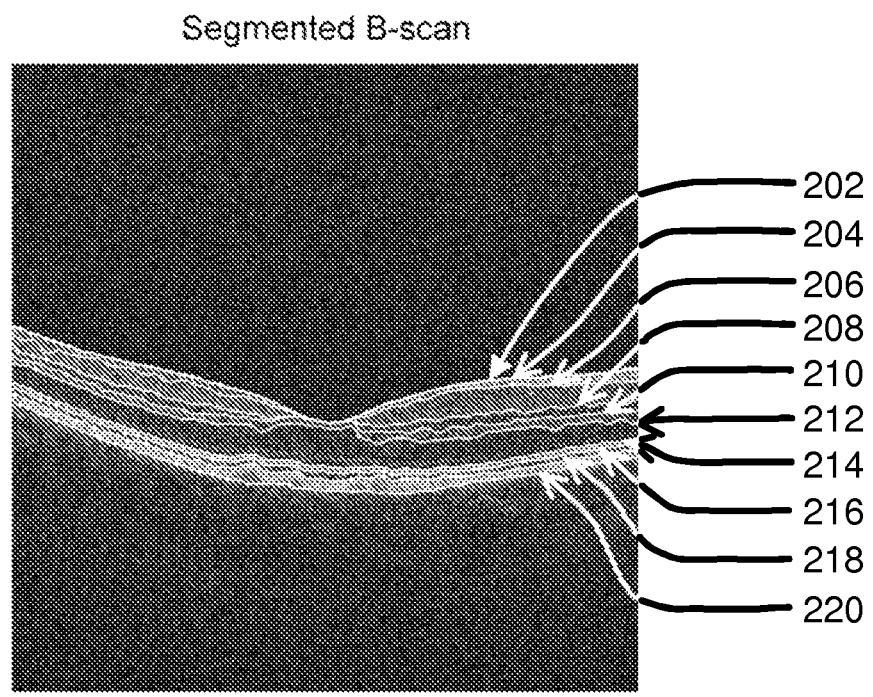
Figure 2C:
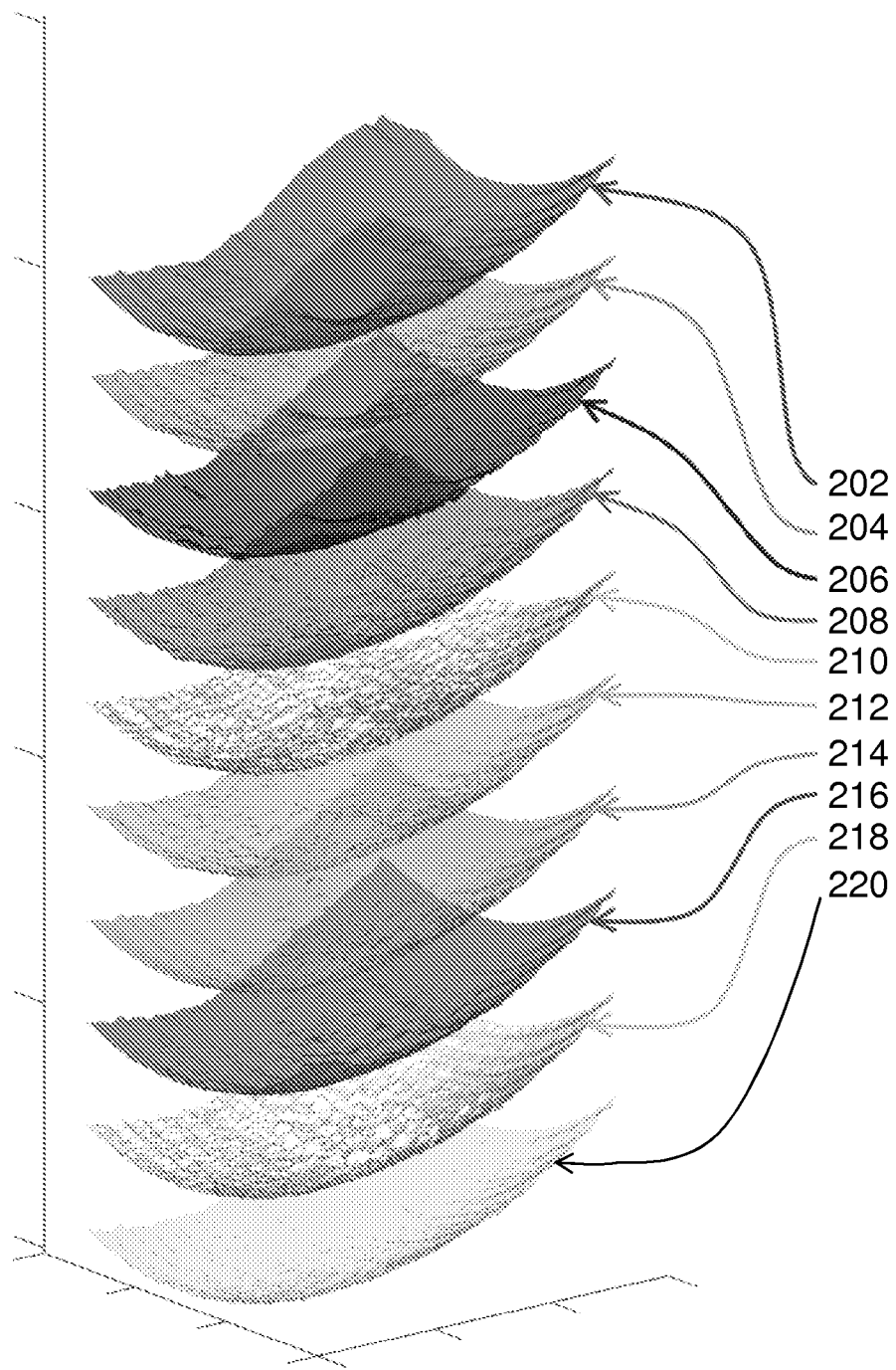
FIG. 2C shows the above-identified 10 separate B-scan segmentations in a perspective view to show that the layers are curved in conformation with the anatomy of the retinal layers.

Referring now to FIGS. 2B and 2C, the layers are indicated as follows: 202: ILM; 204: iRNFL; 206: oRNFL; 208: IPL; 210: INL; 212: OPL; 214: IS; 216: OS; 218: iRPE; 220: oRPE.

Figure 3:
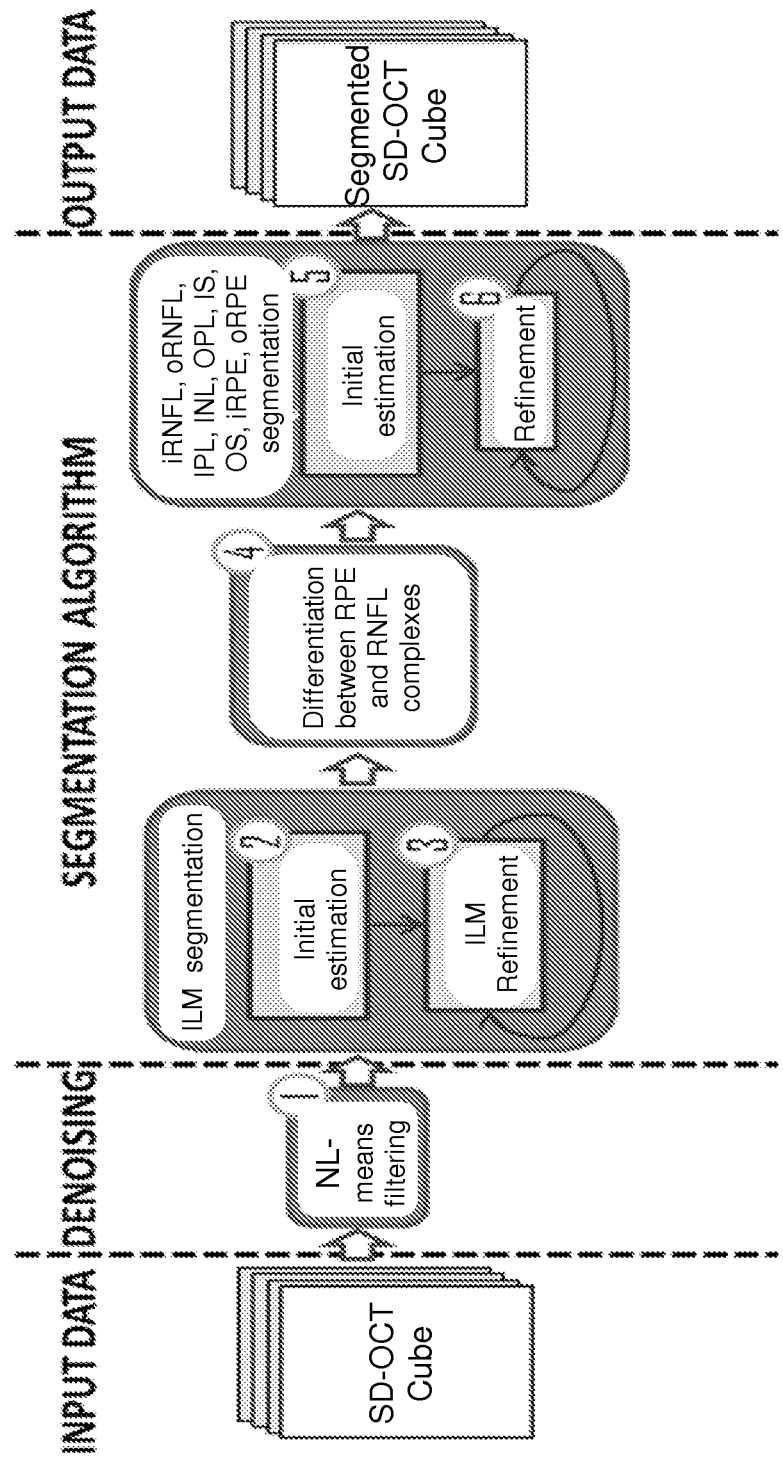
FIG. 3 is a schematic representation of steps used in segmentation the OCT images shown in FIGS. 2A and 2B whereby the various layers ILM, iRNFL, etc. listed in FIG. 2B are identified and stored in a computer file as a segmented SD-OCT cube.

The algorithm is based on an initial estimation of layer boundaries, given intensity and gradient statistics derived from the SD-OCT exam, and an iterative process that updates the segmentation to follow more closely the actual location of each boundary while maintaining a smooth behavior of the segmentation. The key elements of the segmentation method are shown in FIG. 3. The method included a pre-processing denoising step of non-local means filtering (NL-means filtering, labeled as 1 in FIG. 3). The segmentation algorithm starts with the accurate identification of the ILM boundary in a two-step process: An initial estimation of the ILM is determined (labeled as 2 in FIG. 3) and then refined in an iterative process (labeled with 3). Subsequently, the algorithm identifies and differentiates the regions in the cube belonging to the RNFL-complex and the RPE-Complex (4). This differentiation sets up a margin that helps identify an initial estimation of the remaining nine boundaries (5). The initially segmented boundaries are later refined in an iterative process (6), similarly as done for the ILM refinement, but where the updated boundary of each layer also depends on the location of the other eight given a set of constraints.

The initial estimation of the layer boundaries is carried out following pixel intensity and gradient statistics with a set of pre-defined rules derived from retinal physiology information known a priori—order of appearance of the layers in the axial direction and the constraint that the layers should not cross each other—common to every eye. The iterative refinement of the layer boundaries employs this same set of pre-defined rules (constraints) in layer ordering and a weighted median (WM) filter, which was formulated and adapted to the particular case of retinal layer segmentation in SD-OCT cubes. In each iteration step, the estimated boundaries are filtered and updated given this set of constraints. The filtering weights in the WM filter are derived from the gradient information of nearby axial locations, so as to produce a continuous surface that follows the gradient peaks with a given direction while maintaining a smooth behavior. Estimated boundaries are also "flattened" before the WM filtering operation in each iteration step, following a smooth spline fit and later remapped to their corresponding axial location inverting the flattening process after the filtering operation, so as to reduce the staircase effect typically produced by repeated median filtering. The iterative process is set to stop when the layer segmentation reaches a stable solution and no changes over a pixel axial size are introduced to a boundary after a new iteration.

Drusen are degenerative nodular formations located mainly in Bruch's membrane, which separates the retinal pigment epithelium (RPE) from the choroid. Here, the inner and outer boundaries of the RPE are segmented into the iRPE and the oRPE boundaries, respectively. Although Bruch's membrane can difficult to identify in SD-OCT because of the highly reflective RPE adjacent to this layer, drusen appear as RPE deformation or thickening that may form irregularities and undulations as extra-cellular deposits form between the RPE and Bruch's membrane. Further description of histological characterization of drusen may be found in the literature, e.g. Spaide et al. "Drusen Characterization with Multimodal Imaging," *Retina*. 2010 October; 30(9): 1441-1454.

Although the iRPE and oRPE boundaries are the only two boundaries involved in subsequent image processing steps, the determination of the remaining 7 boundaries in this step has proven helpful improving the accuracy and stability of the results, as the segmentation of the iRPE and oRPE boundaries are dependent to the location of the rest of the layers during the iterative process.

3-D Drusen Segmentation

Figure 4:
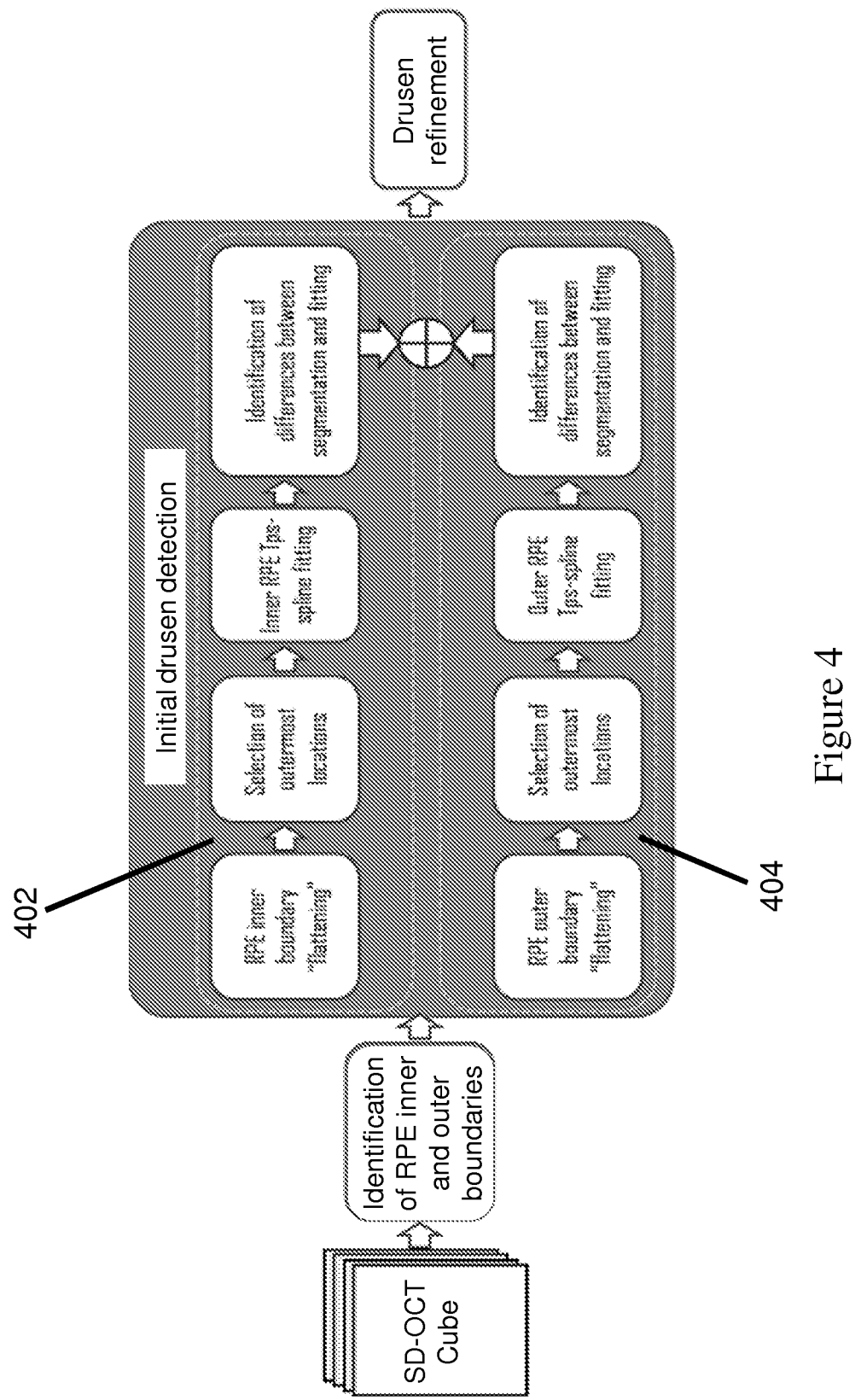
FIG. 4 is a schematic representation of further data processing of the SD-OCT cube obtained from the process of FIG. 3.

Described here is an algorithm that produces accurate automated segmentation of drusen in the SD-OCT volumes using the characterization of the RPE inner and outer boundaries (between the iRPE and the oRPE. layers 218 and 220 in FIG. 2B and FIG. 2C), as obtained in the previous image processing step (3-D retina layer segmentation). The main components of the algorithm are illustrated in FIG. 4, which include an initial drusen detection and further drusen refinement. The characterization of the RPE inner and outer boundaries (as obtained in the previous step) and their particular curvature, reflectivity and topology is employed to identify, segment, and characterize drusen. The main idea behind the algorithm lies in the fitting the segmented RPE boundaries to a thin plate spline (tps-spline) that would preserve the typical curvature of the healthy RPE layer while eliminating the curvatures produced by drusen. Since drusen can be typically observed as small "bumps" in the normal curvature of the RPE, finding the regions between the segmented RPE boundaries and their fitted versions produces an initial drusen characterization. A series of refinement steps follow to help eliminate the regions falsely detected as drusen. These main steps are further described in the following subsections.

Initial Drusen Detection

Figure 5A:
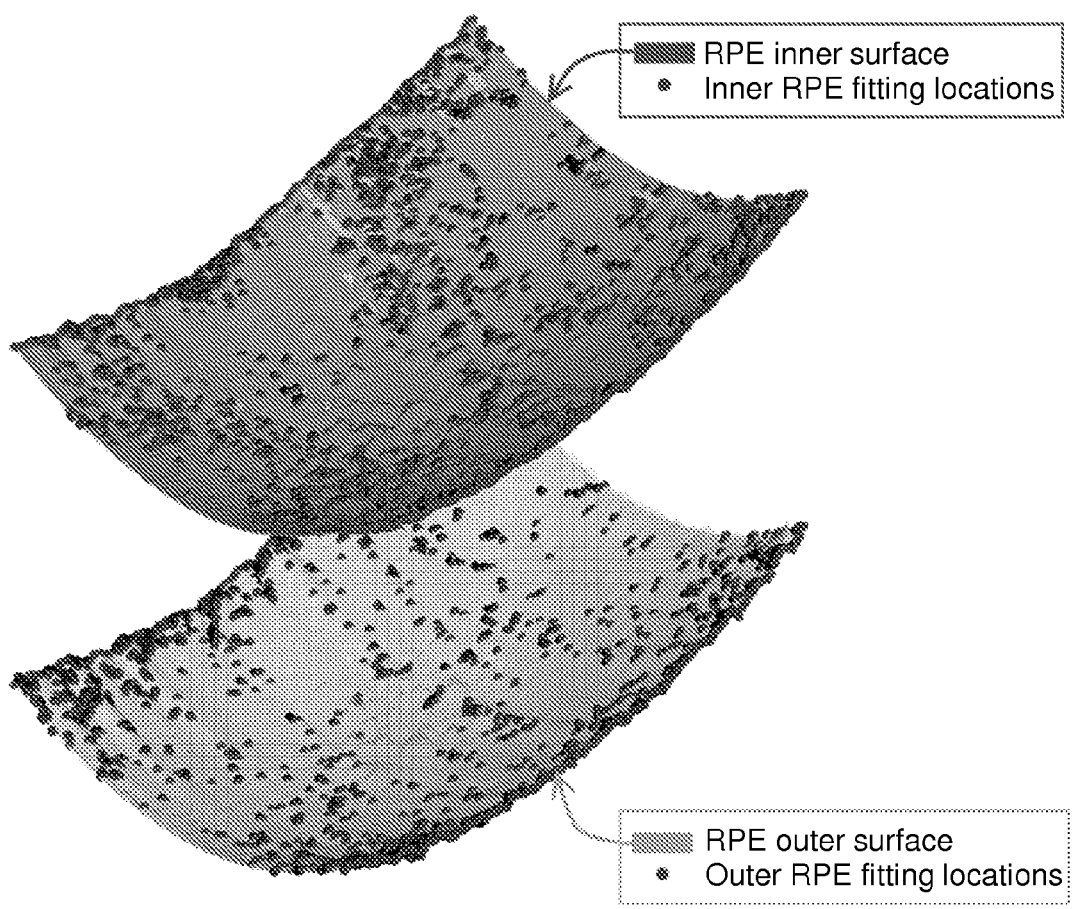
FIG. 5A is a computer generated image of a segment as shown in FIG. 2C, i.e. in a perspective view showing the surface of the inner and outer RPE layers where the anchor locations used to produce a smooth fit of said surfaces are indicated by darkened, raised areas. In the figure, the inner surface of the RPE is above in the perspective view and the RPE outer surface are shown in the bottom perspective view. In practice these layers would be colored by the computer graphics to facilitate human perception of the layers.
Figure 5B:
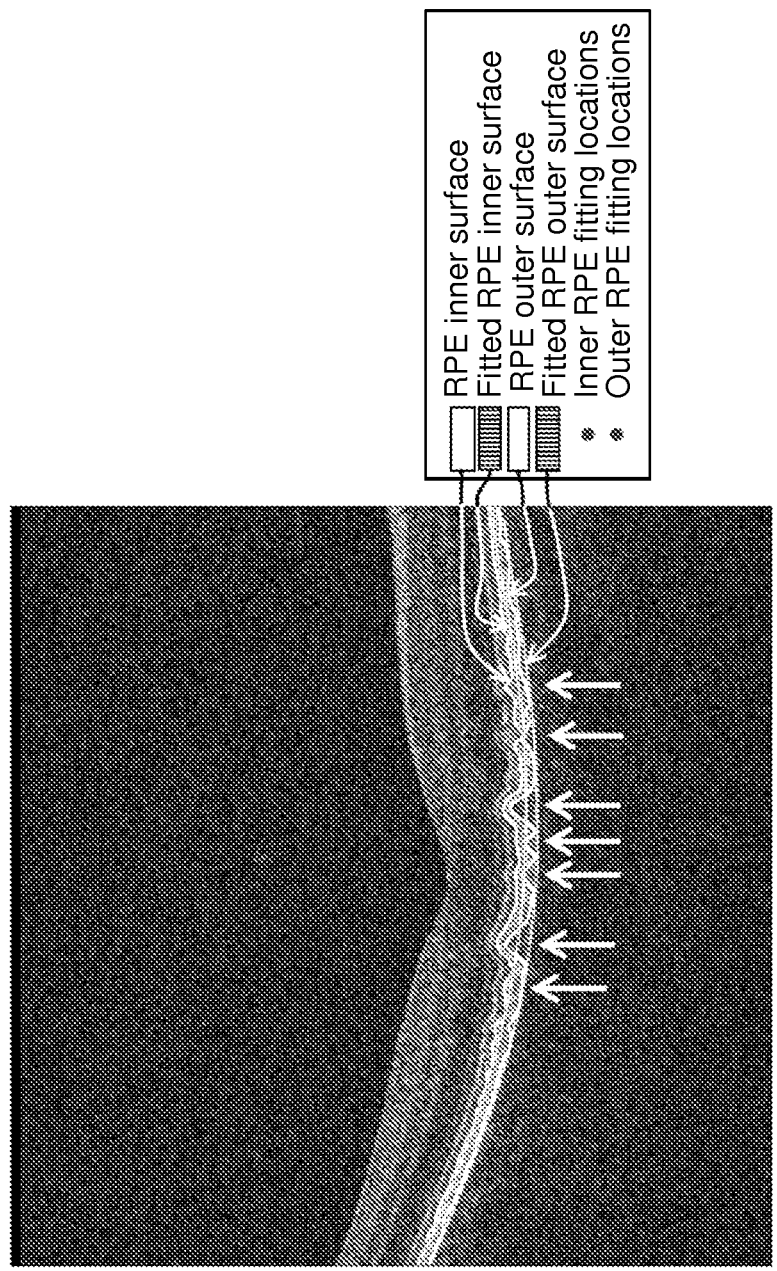
FIG. 5B corresponds to a B-scan view of 5A, and the vertical arrows indicate areas of drusen. The outermost dotted line is the fitted RPE outer surface.
Figure 6B:
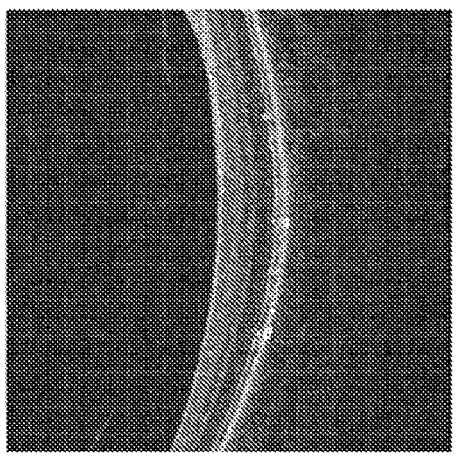
FIGS. 6A, 6B, and 6C is a series of images showing initial drusen segmentation in both en face (frontal section) (FIG. 6A) and 2 B scans (FIGS. 6B and 6C, corresponding to the azimuthal locations as shown by the vertical dotted lines in 6A).
Figure 6C:
Figure 6A:
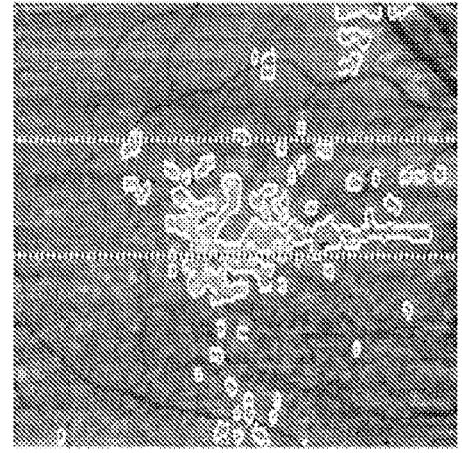

The resulting segmentations of the inner and outer boundaries of the RPE layer are processed following the same process for each boundary independently. The main idea behind this process is fitting a surface that follows its outermost locations of a boundary (lower locations as represented in the B-scan, with higher axial value) and smoothes out the presence of the "bumps" that indicate drusen (FIG. 5B, with drusen indicated by arrows). Drusen can then be identified as the regions located between the segmented boundary and this fitted surface. The steps in obtaining a fitted surface of these characteristics are indicated in FIG. 4 and examples of resulting surfaces are illustrated in FIG. 5A: The method first selects a set of candidate locations from the segmented boundary were a thin-plate spline surface (tps-surface) is fitted. The candidate locations that are selected are those in the RPE boundary that are most likely not affected by drusen (or possible RPE detachment) and follow a normal healthy RPE curvature, by selecting those locations following a convex shape in the extent of each B-scan. Two different tps-surfaces are then fitted to the candidate locations selected for the inner and outer RPE boundaries, respectively. A visual example of the original surfaces, fitted surfaces and selected candidate points is shown in FIGS. 5A and 5B. The initial drusen segmentation is formed by the regions located either between the segmented inner RPE boundary and its corresponding fitted surface or the outer boundary and its corresponding fitted surface, where the separation is larger than a threshold determined by the statistics of the differences between those layers, respectively. Such threshold was determined by finding the first local maximum in the histogram of the recorded separation values in each axial direction. The reasoning behind this threshold value is that it is expected to find a large number of low separation locations due to fitting differences (noise) and not caused by the presence of drusen. The analysis also imposed the constraint that only those regions also presenting a peak difference between the segmented boundaries and their tps-surface fitting of at least 10 μm are considered as druse candidates. An example of the resulting initial drusen segmentation can be observed in FIG. 6A-6C.

Drusen Refinement

Falsely initially-detected drusen are removed from the segmentation results in a series of refinement steps based on the shape, reflectivity and gradient characteristics expected in drusen. The method considers a minimum drusen extent of 45 microns in the azimuthal direction (what is approximately the standard protocol distance between B-scans for SD-OCT images taken in the macula region), so drusen regions with a lower extent (following three-dimensional 8-neighbor connection) were removed from the segmentation as a likely false positive detection. The remaining detected drusen are then further refined by considering the intensity and shape characteristics of each detected region. To enhance conspicuity of detected drusen, a drusen projection image (RSVP image) is computed by "filling" the voxel values of detected drusen candidate regions with the maximum intensity value of their corresponding A-scans in the RPE vicinity (region between segmented inner RPE and fitted outer RPE), and later adding the cube voxel values in the axial direction, producing and en face image. Each detected drusen region is also projected onto the image projection plane. Those regions in the projected image in which the difference between their average intensity and their surrounding background neighborhood (pixels in the vicinity of the region not belonging to initially segmented drusen) is relatively low, or the ratio of the lateral and azimuthal dimensions is larger than 6, were also considered a false positives and removed from the segmentation results. The reasoning behind the intensity constraint is that intensity differences are expected due to the "lifting" of the RPE in the presence of drusen, while the dimensions constraint is applied, since the projected drusen regions are expected to have comparable dimensions in both directions.

Figure 6E:
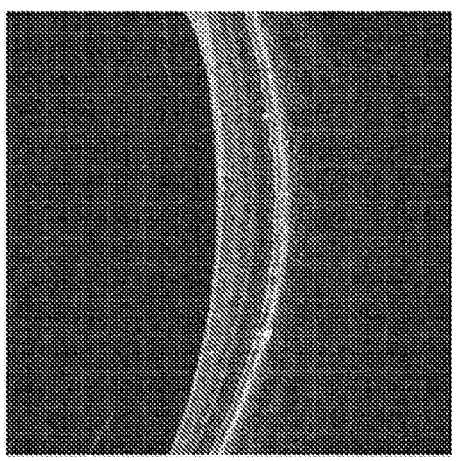
FIGS. 6D, 6E, and 6F is a series of images showing the drusen segmentation after the refinement step for the same example and views as shown in 6A, 6B, and 6C, respectively.
Figure 6F:
Figure 6D:
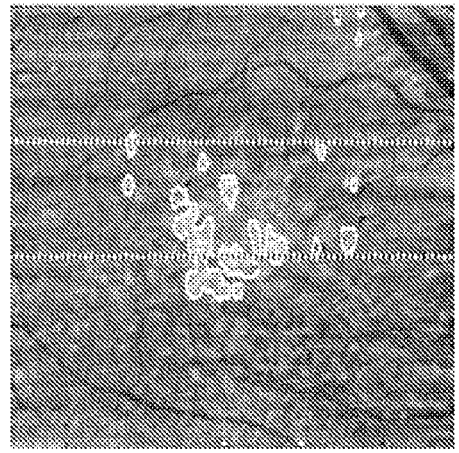

The segmentation of the resulting regions positively identified as drusen is then smoothed to provide less coarse results. The axial projection of each region volume is smoothed with a Gaussian filter (0.02 mm of standard deviation) and then remapped into the three dimensional space considering its baseline, indicated by the outer PRE boundary surface fitting. An example segmentation after these refinement steps can be observed in FIG. 6D-6F.

(3) Feature Extraction

The method comprises a measurement of up to 26 clinical and SD-OCT imaging features ($F_1$-$F_{26}$) per patient eye, acquired from the patient data collected at the clinical visit and from previous patient visits and the known patient history (list of features and short description indicated in Table 1). Two of this features, $F_1$ and $F_2$, relate to the patient demographics, indicating patient age and gender, respectively. Another two of this features, $F_3$ and $F_4$, relate to AMD status in the contralateral eye, indicating the presence of wet AMD in the contralateral eye and the progression through time of wet AMD in the contralateral eye, respectively. The remaining 22 features, $F_5$ to $F_{26}$ relate to drusen characteristics extracted from the collected SD-OCT images of each particular patient eye obtained through processing of the segmented drusen location and extent within the images. 11 of the features, $F_5$ to $F_{15}$, are extracted directly from the SD-OCT image acquired at clinical visits, while the remaining 11, $F_{16}$ to $F_{26}$, are computed by analyzing the progression through time of those same features, considering previously acquired data for each particular eye.

TABLE 1

Features considered in progression model

| Feature | Description |
|---|---|
| $F_1$ | Age of the patient at clinical visit (in months) |
| $F_2$ | Gender of the patient: Coded as 0 for male and 1 for female |
| $F_3$ | Presence of wet AMD in contralateral eye at clinical visit: Coded as 0 for non-present and 1 for present. |
| $F_4$ | Slope of linear fit through time of $F_3$ considering all patient SD-OCT imaging history (in 1/months) |
| $F_5$ | Number of drusen separated regions in SD-OCT at clinical visit |
| $F_6$ | Mean volume per drusen separated region in SD-OCT at clinical visit (in $mm^3$/drusen region) |
| $F_7$ | Total measured volume of drusen regions in SD-OCT at clinical visit (in $mm^3$) |
| $F_8$ | Mean en face (axial projection) area per drusen separated region in SD-OCT at clinical visit (in $mm^2$/drusen region) |

TABLE 1-continued

Features considered in progression model

| Feature | Description |
| --- | --- |
| $F_9$ | Total measured en face (axial projection) area of drusen regions in SD-OCT at clinical visit (in $mm^2$) |
| $F_{10}$ | Area of drusen affected region in SD-OCT at clinical visit (convex hull of detected en face drusen region) (in $mm^2$) |
| $F_{11}$ | Drusen density in affected area ($F_9/F_{10}$) in SD-OCT at clinical visit |
| $F_{12}$ | Maximum height of drusen measured in SD-OCT at clinical visit (in mm) |
| $F_{13}$ | Average slope of detected drusen in SD-OCT at clinical visit. |
| $F_{14}$ | Mean value of pixel intensity (reflectivity) inside drusen regions, measured from normalized SD-OCT cube at clinical visit (cube normalized to take values from 0 to 1) |
| $F_{15}$ | Standard deviation of pixel intensity (reflectivity) inside drusen regions, measured from normalized SD-OCT cube at clinical visit (cube normalized to take values from 0 to 1) |
| $F_{16}$ | Slope of linear fit through time of $F_5$ considering all patient SD-OCT imaging history (in 1/months) |
| $F_{17}$ | Slope of linear fit through time of $F_6$ considering all patient SD-OCT imaging history (in $mm^3$/(drusen · months)) |
| $F_{18}$ | Slope of linear fit through time of $F_7$ considering all patient SD-OCT imaging history (in $mm^3$/months) |
| $F_{19}$ | Slope of linear fit through time of $F_8$ considering all patient SD-OCT imaging history (in $mm^2$/(drusen · months)) |
| $F_{20}$ | Slope of linear fit through time of $F_9$ considering all patient SD-OCT imaging history (in $mm^2$/months) |
| $F_{21}$ | Slope of linear fit through time of $F_{10}$ considering all patient SD-OCT imaging history (in $mm^2$/months) |
| $F_{22}$ | Slope of linear fit through time of $F_{11}$ considering all patient SD-OCT imaging history (in 1/months) |
| $F_{23}$ | Slope of linear fit through time of $F_{12}$ considering all patient SD-OCT imaging history (in mm/months) |
| $F_{24}$ | Slope of linear fit through time of $F_{13}$ considering all patient SD-OCT imaging history (in 1/months) |
| $F_{25}$ | Slope of linear fit through time of $F_{14}$ considering all patient SD-OCT imaging history (in 1/months) |
| $F_{26}$ | Slope of linear fit through time of $F_{15}$ considering all patient SD-OCT imaging history (in 1/months) |

It is desirable in the method to extract a large number of features from drusen present in SD-OCT images to comprehensively characterize the AMD disease process and that can be useful in predicting disease progression. The present methods are used to extract such features from the three-dimensional drusen segmentations derived from SD-OCT, including characteristics of drusen shape and geometry, total drusen en face area, 3D volume of drusen, total number of drusen, mean area and volume per detected drusen region, maximum drusen height, extent of retinal area affected by drusen, drusen density in affected area, drusen slope, drusen reflectivity, and texture properties in the area delimited by drusen (mean and standard deviation of reflectivity inside drusen). Standard deviation is calculated by well-known computational methods. As known, it is a measure of the dispersion of a set of data from its mean. The more spread apart the data, the higher the deviation. Standard deviation is calculated as the square root of variance.

This set of features is extracted from the SD-OCT cube of each patient and eye at each clinical visit, corresponding to an eye examination in a particular date and time ($F_5$-$F_{15}$). Maximum drusen height may be defined as a single value in a single image representing the highest length of a druse in a longitudinal scan (e.g. B scan). In order to capture the possible information in disease status that may be characterized by the evolution of these quantitative features over time, the method includes an evolution measurement for each of these quantitative features, coded as separate progression features ($F_{16}$-$F_{26}$). These evolution measurements are computed by considering their corresponding quantitative features extracted from previous SD-OCT exams of the same patient and eye (those exams taken at a previous date) and fitting their value over time using a linear function (in the future other functions such as non-linear could be used). The slope of each resulting function fitted to the longitudinal data acquired for each feature constitutes an independent progression feature. That is, each eye is characterized by the features extracted at the patient clinical visit and their respective increase (or decrease) over time, taking in consideration previous SD-OCT scans from the same patient and eye. The complete list of features used in the prediction model is enumerated in Table 1. Below is a description of the process considered to extract the significant imaging features using the segmentations obtained from previous image processing steps:

$F_5$: A number of drusen separate regions is computed by finding the separate outlined regions by the previous drusen segmentation step. We first generate a three dimensional matrix of the same dimensions as the collected SD-OCT image, which is defined as drusen mask matrix, populated with 0's for the values outside the segmented drusen regions and 1's inside the segmented drusen regions. The number of separate regions containing values of 1 (following a 8-connection neighborhood in the lateral-azimuthal plane) that can be identified in the drusen mask matrix constitutes the feature value.

$F_6$: The mean volume of the drusen separate regions can be computed dividing the total drusen volume, computed by adding the number of 1's in the drusen mask matrix (as defined in F5) multiplied by the voxel dimensions in the SD-OCT images, by the number of drusen separate regions F5. Such result constitutes this feature value.

$F_7$: The feature value represents the total drusen volume, computed by adding the number of 1's in the drusen mask matrix (as defined in F5) multiplied by the voxel dimensions in the SD-OCT images.

$F_8$: A 2-Dimensional matrix, which is defined as RSVP mask, is generated by adding the values of the drusen mask matrix in the axial (depth) axis. The mean en face area per drusen region is computed by dividing the total drusen en face area, computed by adding the number of positive values in the RSVP mask multiplied by the lateral and azimuthal voxel dimensions in the SD-OCT images, by the number of drusen separate regions $F_5$. Such result constitutes this feature value.

$F_9$: The feature value represents the total en face drusen area, computed by adding the number of positive values in the RSVP mask (as defined in F8) multiplied by the lateral and azimuthal voxel dimensions in the SD-OCT images.

$F_{10}$: A drusen extent mask matrix is generated by computing the convex hull of the positive values of the RSVP mask (as defined in F8). The feature value represents the total en face area of drusen affected region, computed by adding the number of positive values in the extent mask matrix multiplied by the lateral and azimuthal voxel dimensions in the SD-OCT images.

$F_{11}$: The feature value is computed by dividing the total en face drusen area ($F_9$) by the total en face area of drusen affected region ($F_{10}$) and represents a measurement of drusen presence density in the extent of drusen affected area.

$F_{12}$: The feature value indicates the maximum height of detected drusen, which can computed by finding the maximum value in the RSVP mask (as defined in F8). In the future, the average and standard deviation of drusen regions height will be also computed.

$F_{13}$: The feature value represents the average slope of the drusen segmentations, computed by the average gradient of the nonzero regions in the RSVP mask (as defined in F8).

$F_{14}$: This feature represents the mean intensity recorded in the SD-OCT scans inside drusen regions. The SD-OCT cube is initially normalized to take values from 0 to 1. The normalized values in the cube corresponding to regions populated with 1's in the drusen mask matrix (as defined in F5) are collected and their mean value constitutes this feature value.

$F_{15}$: This feature represents the intensity deviation recorded in the SD-OCT scans inside drusen regions. The SD-OCT cube is initially normalized to take values from 0 to 1. The normalized values in the cube corresponding to regions populated with 1's in the drusen mask matrix (as defined in F5) are collected and their standard deviation value constitutes this feature value.

(4) Computation of Risk Score Using Extracted Features and Clinical Data

A prediction model produces a score indicating the likelihood of AMD progression at a given elapsed time since a patient clinical visit, considering the quantitative imaging features, presence of wet AMD in the fellow eye, patient demographics (age and gender), and the time elapsed between the longitudinal observations from the same patient and eye, as previously specified. Time elapsed since the clinical visit, at which a prediction is made, is taken into consideration when computing a risk of progression score as a patient chance of progression increases with time.

This may also include a genetic predisposition to AMD. The genetic predisposition may be obtained by family history or genetic markers such as Complement factor H (CFH), complement factor B (CFB)/complement component 2 (C2), LOC387715/ARMS2 and HTRA1, which are believed to be responsible for the majority of heritable AMD risk.

Complement factor H SNP Y402H (rs1061170) on chromosome 1q32 was the first major susceptibility gene discovered for AMD and could be responsible for 50% of AMD risk. The CFH gene codes for a glycoprotein that regulates the alternative complement pathway and binds to Bruch's membrane. The Y402H SNP can result in abnormal complement activation and host cell destruction secondary to ineffective binding to Bruch's membrane. CFH Y402H promotes the development of early AMD (drusen formation) and progression to advanced AMD, and can act synergistically with smoking history to increase one's risk of wet AMD. Presence of these mutations is factored, in certain embodiments, in the calculation of the risk score.

The risk score was formulated to be the chances of progression within a given future time using an L1-penalized Poisson model with logarithm of time-to-prediction as an offset, and with imaging features and clinical parameters as predictors. To make the model more flexible, it allows piecewise-linear functions by using an expanded basis for each imaging feature, with hinge functions which had knots at the sample deciles (estimated from training data). A risk score at an elapsed time t since the clinical visit is computed using the following formula:

$$S(t) = e^{(\beta_0 + \sum_{m=1}^{26} \beta_m(F_m) F_m)} \cdot t,$$

where the coefficients $\overline{\beta}(F) = [\beta_0, \beta_1(F_1), \beta_2(F_2), \ldots, \beta_{26}(F_{26})]$ are weights associated to each corresponding feature value. The dependence of the weights with each associated feature value corresponds to the piece-wise linear nature of the model. The particular weight functions are determined through machine learning process (such as piecewise linear regression) on a training dataset.

(5) Output: Patient Stratification

Each eye is categorized by its risk of progression to wet AMD at time t since the clinical visit, either as high-risk or low-risk, depending whether its computed risk score S (t) is over or under a selected threshold T, respectively:

$$\text{Category}(t) \begin{cases} \text{High-risk} & \text{if } S(t) \geq T \\ \text{Low-risk} & \text{if } S(t) < T \end{cases}.$$

The threshold T is determined by selecting desired sensitivity or specificity rates of progression detection in a training dataset.

Initial Evaluation

Data Collection

Retrospective data was collected from 330 eyes in 244 patients at Stanford University Vitroretinal Clinic, comprising a total of 2146 longitudinal SD-OCT exams obtained over a 5 year time interval. The exams were obtained from consecutive patients that were diagnosed with AMD in their first clinic visit, and analyzed by an SD-OCT system (CirrusOCT; Carl Zeiss Meditec, Inc., Dublin, Calif.). No other exclusion criteria were considered. The research was approved by the institutional Human Subjects Committee and followed the tenets of the Declaration of Helsinki. Out of the collected 330 eyes, 36 showed progression from dry to wet AMD over time (31 patients), 150 maintained their dry status (97 patients), and 106 were diagnosed with wet AMD from the beginning of the study (93 patients). Patients with a dry AMD diagnosis in an initial visit and at least one more follow up visit with an either dry or wet diagnosis were of interest when evaluating progression (first two columns in Table 2). Group-based demographics are summarized in Table 2.

or interval censoring (time between a previous dry diagnosis and a follow-up diagnosis indicating wet AMD) were excluded. This analysis was conducted in the preliminary data as described above, with a dependence of number of patients, eyes, and observations with tested time for AMD progression as described in Table 2. For this example, the

TABLE 2

Patient demographics and number of eyes and visits of the collected dataset employed in the preliminary evaluation.

|  | Dry status throughout study | Progressed from dry to wet AMD throughout study | Single visit with dry AMD | Wet AMD at beginning of study | Overall |
|---|---|---|---|---|---|
| Patients, number | 97 | 31 | 23 | 93 | 244 |
| Eyes, Number | 150 | 36 | 38 | 106 | 330 |
| Number of visits per eye, mean (SD) | 4.33 (3.11) | 3.92 (2.95) | 1 (0) | 7.35 (5.67) | 6.43 (5.36) |
| Months between visits, mean (SD) | 6.28 (5.77) | 5.65 (4.90) | — | 4.40 (4.43) | 4.82 (4.93) |
| Gender, % Female | 55.01% | 68.79% | 80.00% | 65.22% | 72.03% |
| Age at visits (years), mean (SD) | 78.19 (9.83) | 83.26 (5.99) | 79.80 (11.47) | 81.58 (7.19) | 80.98 (8.05) |
| | Maintained dry status for: No. Dry Obs./Eyes/Patients | | | | |
| 6 months | 649/150/104 | 77/22/16 | — | — | — |
| 12 months | 647/150/104 | 48/18/13 | — | — | — |
| 18 months | 633/150/104 | 32/14/10 | — | — | — |
| 24 months | 587/149/103 | 16/7/5 | — | — | — |
| 30 months | 541/146/100 | 9/3/2 | — | — | — |
| 36 months | 470/142/96 | 7/2/2 | — | — | — |
| 42 months | 412/140/94 | 4/2/2 | — | — | — |
| 48 months | 325/134/89 | 0/0/0 | — | — | — |
| | Progressed within: No. Dry Obs./Eyes/Patients | | | | |
| 6 months | 0/0/0 | 9/7/7 | — | — | — |
| 12 months | 0/0/0 | 27/14/13 | — | — | — |
| 18 months | 0/0/0 | 50/23/20 | — | — | — |
| 24 months | 0/0/0 | 63/24/20 | — | — | — |
| 30 months | 0/0/0 | 75/27/22 | — | — | — |
| 36 months | 0/0/0 | 97/31/26 | — | — | — |
| 42 months | 0/0/0 | 106/33/28 | — | — | — |
| 48 months | 0/0/0 | 114/34/29 | — | — | — |

All the SD-OCT scans were acquired using an instrument that produced an imaging volume with dimensions of 6 (lateral)×6 (azimuthal)×2 (axial)–mm with voxel dimensions of approximately 12, 47 and 2-μm respectively (512, 128, and 1024 voxels in each direction, respectively). The raw data produced by the SD-OCT instrument were imported into the vendor's proprietary software for analysis and reconstruction (Zeiss Research Browser, version 6.0.2.81, Carl Zeiss Meditec, Inc., Dublin, Calif.) and later exported to files describing the reflectivity measured at each voxel location with 8-bit precision. All the data processing and methods were later implemented and carried out using Matlab (The MathWorks, Inc., Natick, Mass.).

Statistical Analysis of Extracted Features

To develop the model, the statistical differences were investigated (a) in each of the extracted quantitative image features, (b) AMD diagnosis in contralateral eye, and (c) patient demographics and factors ($F_1$-$F_{26}$, established in description) between the cohort of observations presenting AMD progression within a given elapsed time since clinical visit versus the cohort that remained dry within the same time. Those observations in which there was not absolute certainty of the eye's AMD status at the tested time either due to right-censoring (time after last known dry diagnosis and there is no future information known about the patient) analysis of conversion was chosen within a 12 month interval since clinical visit as representative, with mean and standard deviation of each analyzed feature as reported in Table 3. Next, we analyzed the statistical significance of each feature between progressing and non-progressing observations using a mixed-effects analysis of variance (Anova), where AMD status is a fixed effect and the particular patient and eye is a random effect. The Anova p-values were corrected using a multiple hypothesis testing analysis by estimating the false positive discovery rate q-values considering all tested features. The distribution differences between the progressing and non-progressing cohorts were analyzed for each feature, and those presenting a q-value under 0.05 were considered statistically significant. The q-values resulting from testing the distribution differences between those observations that progressed and those that did not progress within 12 months are summarized in Table 3. Apart from patient's age, none of the other extracted features presented significant statistical differences between progressing and non-progressing observations within 12 months of a clinical visit.

TABLE 3

|  | Non-progressing within 12 months Mean (standard deviation) | Progressing within 12 months Mean (standard deviation) | Comparison q-value |
|---|---|---|---|
| $F_1$ | 941.72 (115.98) | 1017.7 (56.23) | <0.01 |
| $F_2$ | 0.555 (0.497) | 0.815 (0.396) | 0.79 |
| $F_3$ | 0.450 (0.499) | 0.667 (0.480) | 0.72 |
| $F_4$ | 0.0015 (0.001) | 0.0000 (0.0000) | 0.44 |
| $F_5$ | 7.59 (6.04) | 5.59 (4.65) | 0.44 |
| $F_6$ | 0.0168 (0.0329) | 0.0344 (0.0416) | 0.44 |
| $F_7$ | 0.103 (0.122) | 0.136 (0.137) | 0.58 |
| $F_8$ | 0.451 (0.708) | 0.779 (0.851) | 0.65 |
| $F_9$ | 2.85 (3.03) | 3.31 (3.36) | 0.58 |
| $F_{10}$ | 10.18 (7.97) | 9.50 (7.42) | 0.44 |
| $F_{11}$ | 0.31 (0.24) | 0.35 (0.25) | 0.78 |
| $F_{12}$ | 0.0965 (0.0451) | 0.1102 (0.0432) | 0.72 |
| $F_{13}$ | 0.342 (0.126) | 0.346 (0.097) | 0.72 |
| $F_{14}$ | 0.354 (0.099) | 0.350 (0.090) | 0.44 |
| $F_{15}$ | 0.099 (0.025) | 0.105 (0.023) | 0.62 |
| $F_{16}$ | 0.071 (0.819) | −0.093 (0.404) | 0.44 |
| $F_{17}$ | −0.00004 (0.0055) | 0.0027 (0.0091) | 0.72 |
| $F_{18}$ | −0.0007 (0.0246) | 0.0021 (0.0162) | 0.44 |
| $F_{19}$ | −0.0013 (0.1230) | 0.0642 (0.2184) | 0.72 |
| $F_{20}$ | −0.0162 (0.6606) | 0.0552 (0.3596) | 0.72 |
| $F_{21}$ | 0.0588 (1.5274) | 0.0998 (0.6623) | 0.72 |
| $F_{22}$ | −0.0006 (0.0622) | 0.0057 (0.0211) | 0.72 |
| $F_{23}$ | 0.0000 (0.0061) | 0.0000 (0.0034) | 0.72 |
| $F_{24}$ | 0.0004 (0.0242) | 0.0002 (0.0225) | 0.72 |
| $F_{25}$ | 0.0011 (0.0171) | 0.0068 (0.0154) | 0.44 |
| $F_{26}$ | 0.0000 (0.0042) | 0.0013 (0.0040) | 0.44 |

Prediction Model Evaluation

Figure 7A:
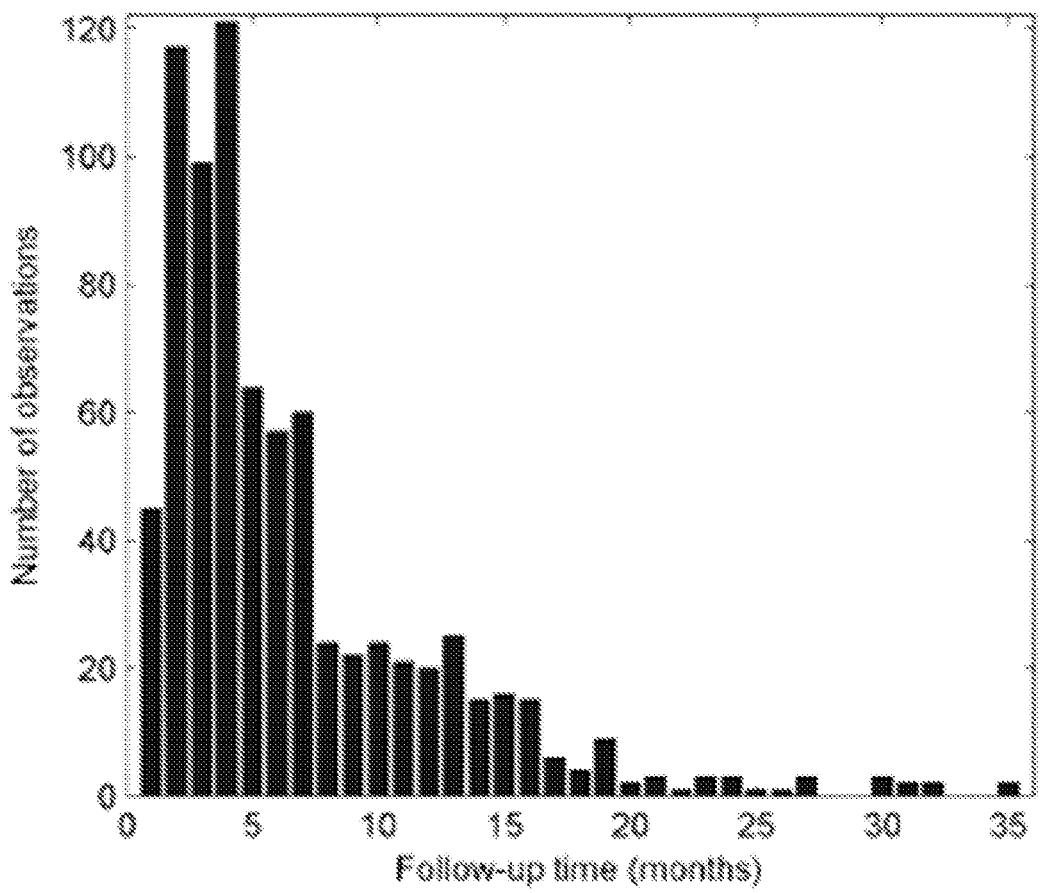
FIGS. 7A, 7B, and 7C are graphs showing data collection for risk calculation and subject classification.

A total number of 790 possible observations from 186 eyes of 128 patients were constructed from the retrospective dataset described above, considering only the clinical visits with a dry AMD diagnosis for each particular eye in the dataset which had at least one follow-up visit for that eye (i.e., that the patient would have either dry or wet AMD at the considered eye at the next time point). The prediction model was trained using the outcomes recorded at each observation's follow-up visit, coded as 1 for observations progressing to wet AMD and 0 for observations maintaining a dry AMD status, both at the considered elapsed time to a follow-up visit. A histogram of the number of constructed observations as a function of time elapsed to a follow-up visit is shown in FIG. 7A. For the evaluations presented below, training and testing of the model was conducted via 10-fold cross-validation, where all observations from the same patient were required to be in the same fold, holding out of the training set those observations from the patients who are being evaluated.

Prediction of Progression Event at Follow-Up

Figure 7B:
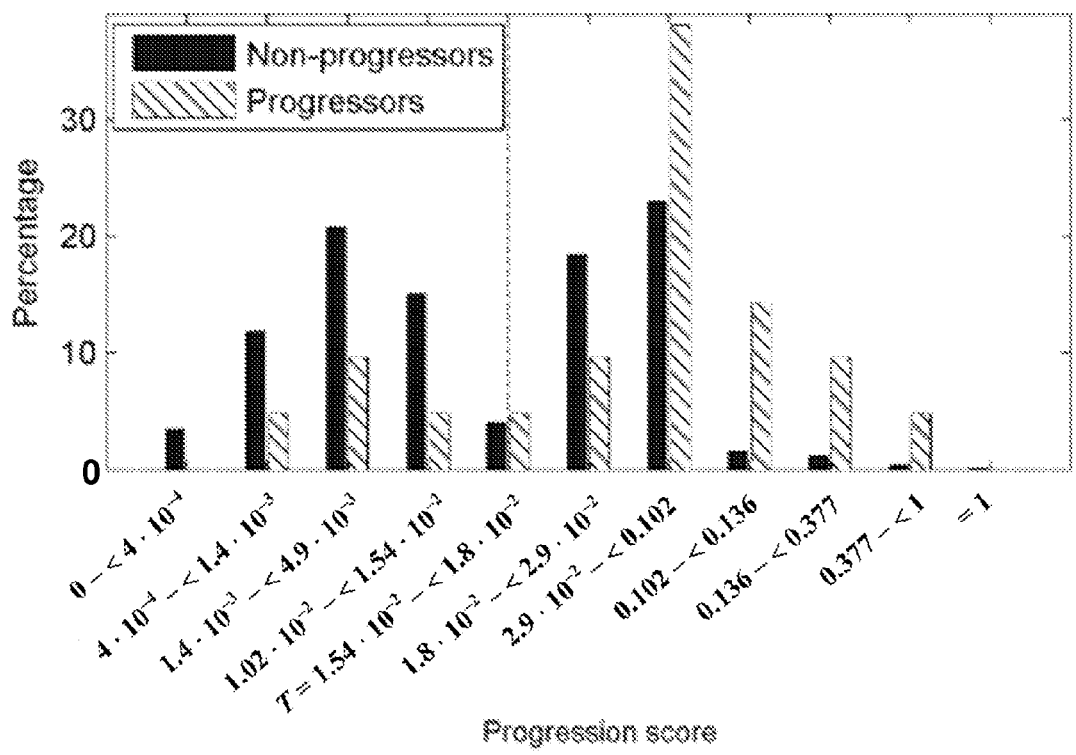
Figure 7C:
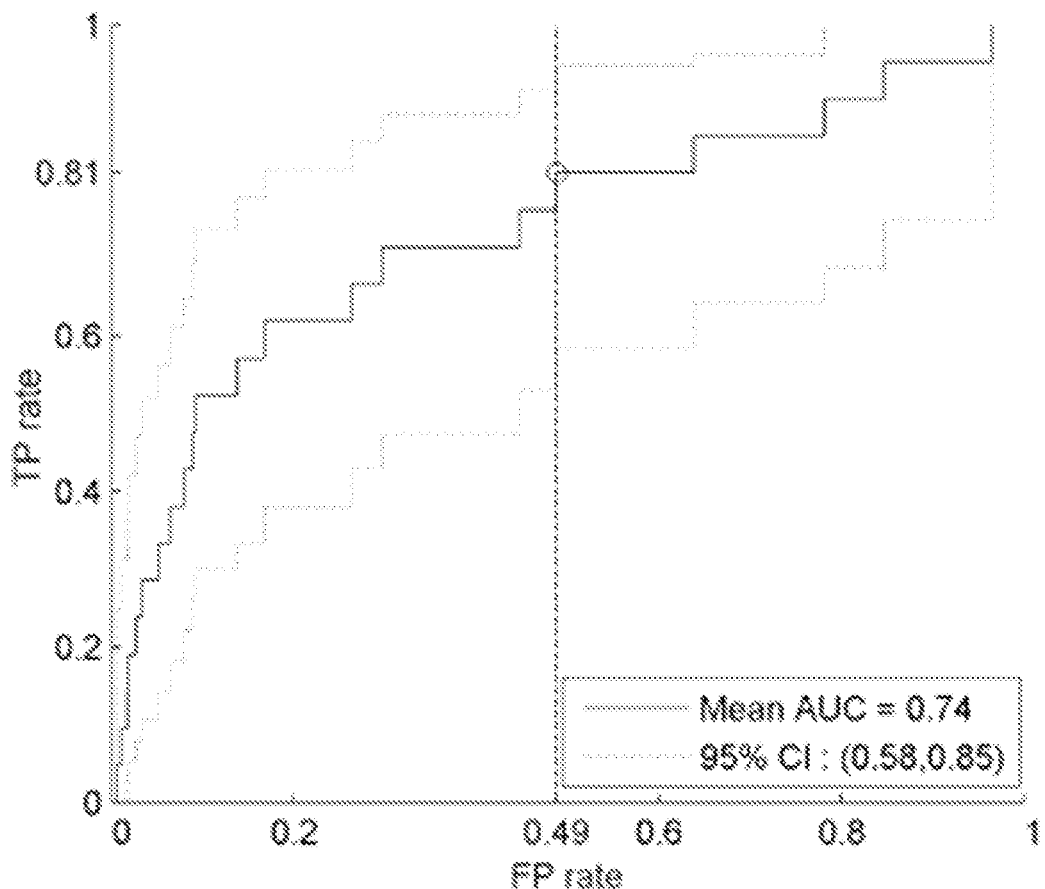

The accuracy of the method for predicting a progression was assessed at follow-up time by constructing a receiver operating characteristic (ROC) curve for the task of discerning eyes which progressed at a follow-up visit from those that maintained a dry status and computing its area under the curve (AUC). The number of observations involved in this evaluation was 790 (from 186 eyes), of which 769 maintained a dry status at a follow-up visit, and 21 progressed to wet AMD at a follow-up visit. FIG. 7B displays the histograms of test observations in which there was AMD progression in the patient's next follow-up visit and those that remained dry as a function of the probability risk score produced by the prediction model. The resulting ROC curve for the model is shown in FIG. 7C, yielding an AUC of 0.74 (0.58, 0.85). Assuming a scoring threshold producing at least 80% sensitivity in the correct prediction of AMD progression ($T=1.54 \cdot 10^{-2}$, as identified in FIG. 7B), the operating point on the ROC curve corresponds to 80.95% sensitivity and 51.24% specificity.

Eye-Based Prediction Evaluation at 12 Months Since Clinical Visit

Figure 8A:
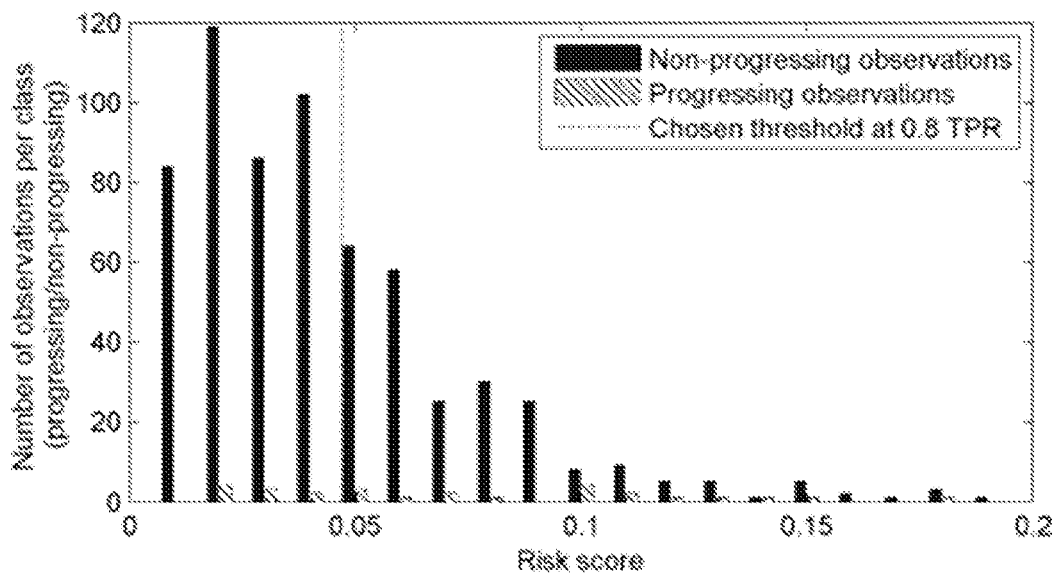
FIGS. 8A, 8B, and 8C is a series of graphs evaluating the performance in making predictions of AMD progression over a 12 month period.
Figure 8B:
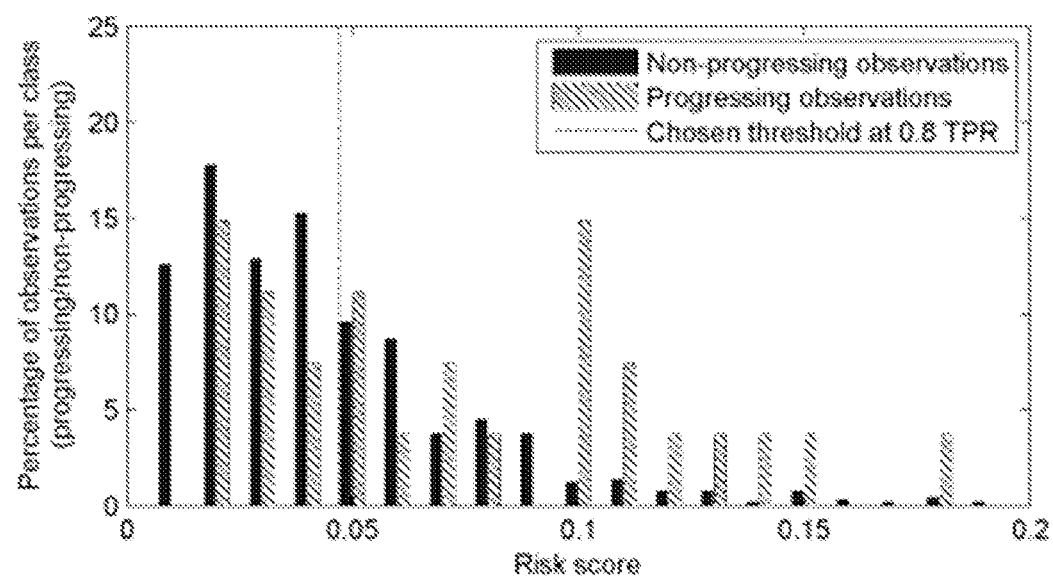
Figure 8C:
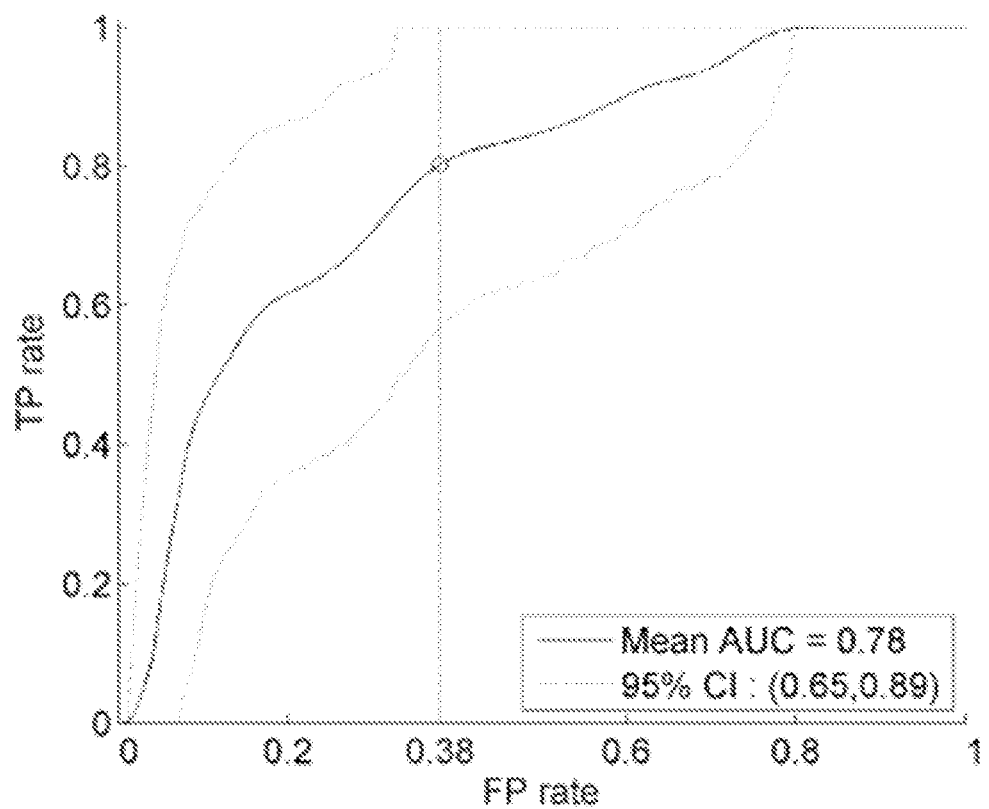

The performance in making a correct prediction of AMD progression per eye at 12 months since a clinical visit was evaluated. Those observations with unknown status at 12 months since a clinical visit (either due to lack of patient follow-up while the patient remained dry or due to a time interval between his/her last dry diagnosis and the first wet diagnosis, in which the progression status was not known) were treated as censored cases (right censoring and interval censoring, respectively). The evaluation identified 721 non-censored observations of such characteristics (from 175 eyes), out of which 27 observations indicated a progression within 12 months (from 14 eyes). The computed risk scores for those observations maintaining a dry status and progressing to a wet status, both within 12 months, is displayed in FIG. 8A. The prediction accuracy per eye testing for progression within 12 months was also assessed by constructing an ROC curve with the eye prediction scores, choosing a random observation per eye from those available in the collected longitudinal data. Mean values and confidence intervals were computed by bootstrapping $10^6$ samples, resampling from the set of available eyes (not censored) with replacement. For each bootstrap sample, a set of eyes were randomly chosen with replacement, and for eyes chosen in the sample a singular observation was randomly chosen from the particular eye available longitudinal data. The number of observations per eye averaged 4.12 (2.97 standard deviation), with a minimum of 1 observation per eye and a maximum of 17 observations. FIG. 8B displays the constructed ROC, with resulting AUC of 0.78 (0.65, 0.89). The cutoff where sensitivity resulted at least of 80% is also identified in the ROC curve, with a particular specificity of 62%. The threshold at such cutoff point was $T=4.71 \cdot 10^{-2}$, and is indicated in FIG. 8A and FIG. 8B.

Figure 9A:
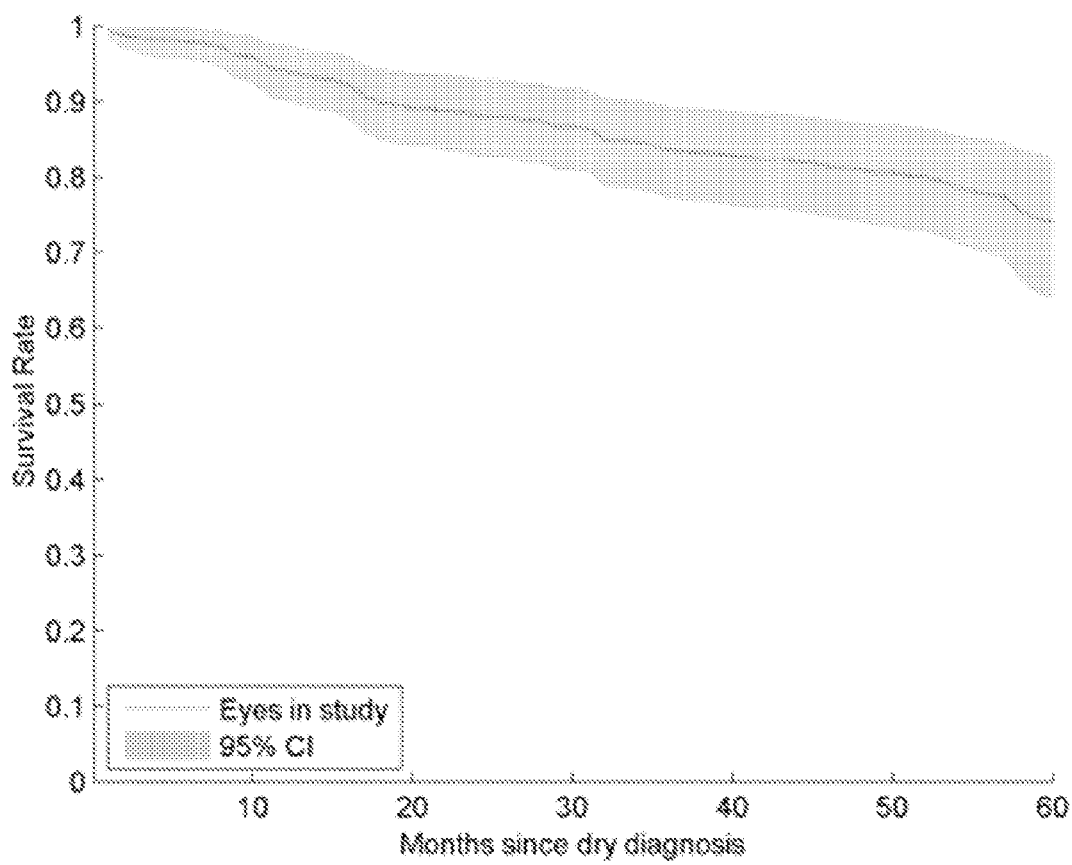
FIGS. 9A and 9B is a pair of survivor curves based on a Kaplan-Meier estimator, where survival rate is considered to be a lack of progression from dry AMD to wet AMD.
Figure 9B:
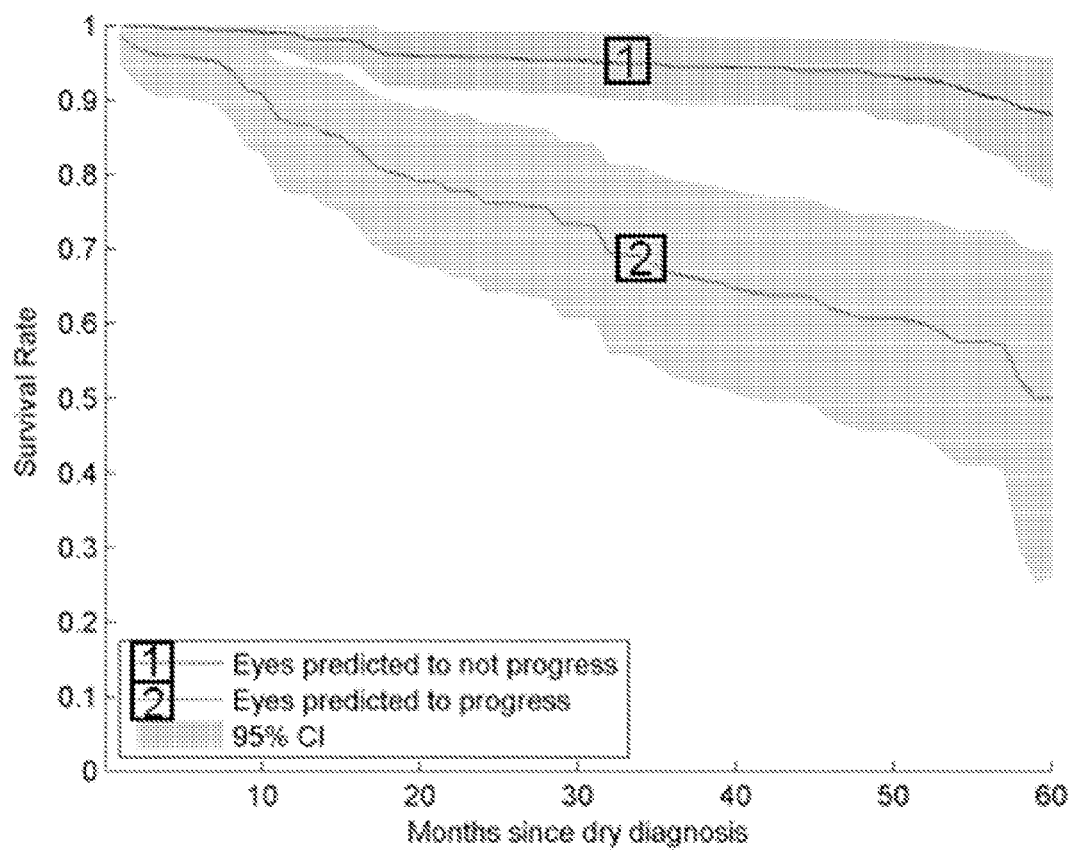
Figure 10A:
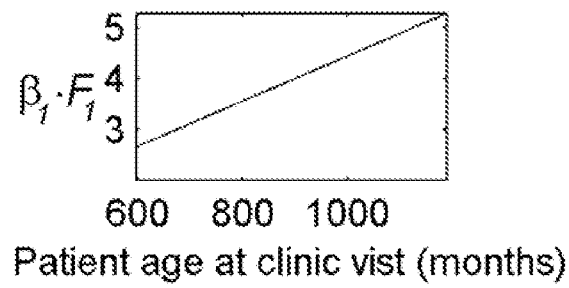
FIGS. 10A, 10B, 10C, 10D, and 10E is a series of graphs showing the weight given to features F1, F2, F12, F15 and F19, respectively. These features are described in Table 1.
Figure 10B:
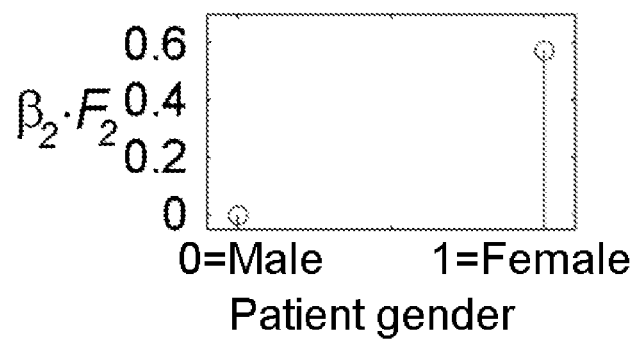
Figure 10C:
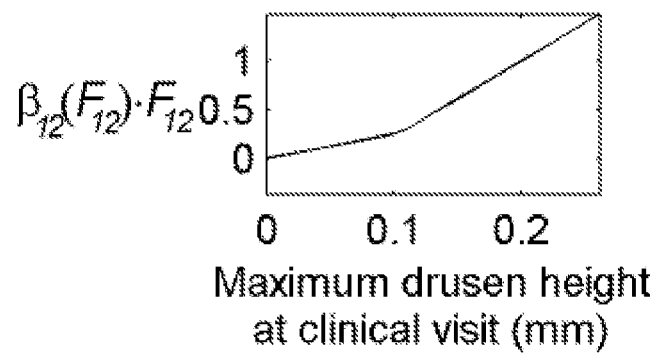
Figure 10D:
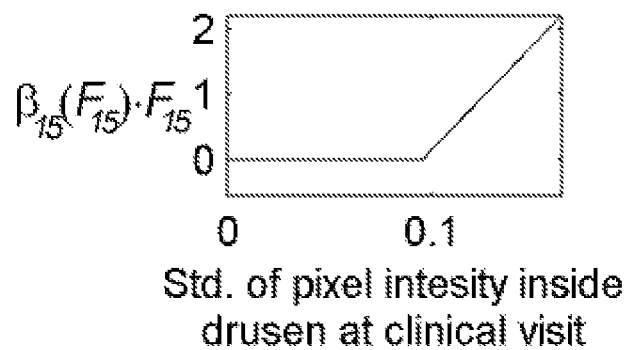
Figure 10E:
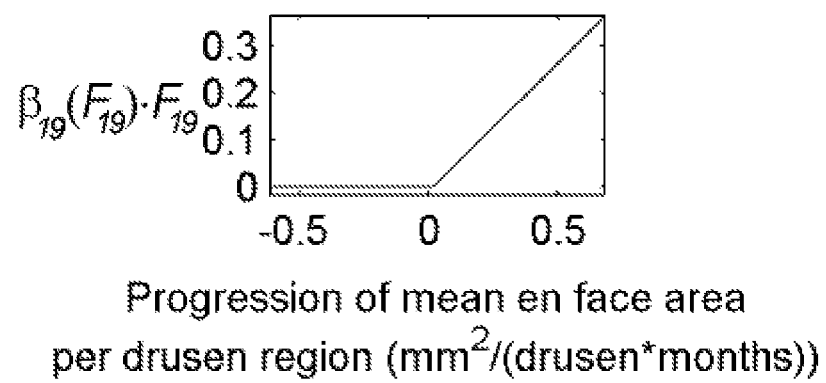

The method also computed the eye-based survival rates of the complete evaluated data, and of those eyes classified as high-risk of progression and low-risk of progression at 12 months since the clinical visit, respectively, using the stratification resulting from the predictive method and threshold as specified above (80% sensitivity, $T=4.71 \cdot 10^{-2}$). Survival rates were computed using the Kaplan-Meier estimator of survival and their mean and 95% confidence intervals were obtained by bootstrapping $10^6$ samples with replacement from the set of eyes, in the same manner as indicated above. FIG. 9A displays the survival rates of all the eyes included in the evaluation and FIG. 9B displays the survival rates for those eyes classified as high risk of progression and low risk of progression testing for progression within 12 months. The results indicate that a mean of 5.93% (with 95% confidence intervals (CI) of (2.42, 9.85)%) of the evaluated eyes progressed within 12 months, and the method was able to stratify patients by their risk of progression at 12 months resulting in a high-risk group with a mean 13.32% ((5.49, 22.70)% CI) progression risk and a low-risk group with a mean 1.16% ((0.00, 3.73)% CI) progression risk, both at 12 months from the clinical visit. Evaluation of the statistical differences in survival rates between eyes labeled as high risk and eyes labeled as low risk by the method via log-rank test yielded a Z value of Z=3.14, indicating statistical significance at 95% in the differences between the two groups (Z>2). It was anticipated that the prediction model could lead to a patient scheduling method where patients with eyes predicted in the low risk category would be assigned to follow-up at 12 months with less than 5% chance of a progression event in such time interval, while patients with an eye predicted in the high risk category would be assigned to follow-up at a shorter time interval, as given by the methods, with a significantly higher chance of progression within 12 months.

Model Building from Collected Training Data

The acquired preliminary dataset was processed in order to determine a set of concrete numerical values for the set of coefficients $\bar{\beta}(F)$. The model was simplified using Lasso regression to what it was found to be the most discriminant features, while maintaining the accuracy presented in the preliminary evaluation. Lasso regularization yielded an optimal lambda value of $\lambda=0.74\cdot10^{-2}$ and the most significant features were: Age ($F_1$), gender ($F_2$) (coded as 0 for men and 1 for women), maximum height of drusen measured in SD-OCT at clinical visit (in mm) ($F_{12}$), standard deviation of pixel intensity in normalized SD-OCT image inside drusen regions at clinical visit ($F_{15}$), and slope of linear fit through time of mean en face area per drusen separated region (in mm$^2$/(drusen·months)) ($F_{19}$). Under this scenario, a risk score can be then computed as:

$$S(t)=e^{(\beta_0+\beta_1 F_1+\beta_2 F_2+\beta_{12}(F_{12})F_{12}+\beta_{15}(F_{15})F_{15}+\beta_{19}(F_{19})F_{19})}\cdot t,$$

with the defined coefficient values:
$\beta_0=-10.8457$
$\beta_1=0.0045$
$\beta_2=0.5732$
$\beta_{12}(F_{12})=2.3813\cdot F_{12}+0.2555\cdot\min((F_{12}-0.0469),0)+1.9498\cdot\min((F_{12}-0.0996),0)+3.2282\cdot\min((F_{12}-0.1113),0)$
$\beta_{15}(F_{15})=32.587\cdot\min((F_{15}-0.0953),0)$
$\beta_{19}(F_{19})=0.5487\cdot\min((F_{19}-0.02),0)$ Pixel intensity may be measured by brightness of images of drusen in an OCT image. The contribution of each of the most discriminant features to the risk score S(t) as a function of the feature values is shown in FIG. 10A-10E, where the horizontal axis represents the feature value ranges observed in the training data.

Thus, the features described above as F1, F2, F12, F15 and F19 can be used to make a prediction of the chances that a patient's AMD in an eye will progress from a dry AMD status to wet AMD within a given time subsequent to a clinical visit.

Using the acquired training data, we selected a threshold value to obtain at least 80% specificity in the predictions for the classification of eyes in high risk or low risk categories of progression at a given future time. This threshold resulted of T=0.0356. Given a computed risk score, we can then classify patients according to their risk following:

$$\text{Category}(t)\begin{cases} \text{High-risk} & \text{if } S(t) \geq 0.0356 \\ \text{Low-risk} & \text{if } S(t) < 0.0356 \end{cases}$$

Use on Subjects at Risk and Relevant Retinal Images

Figure 11:
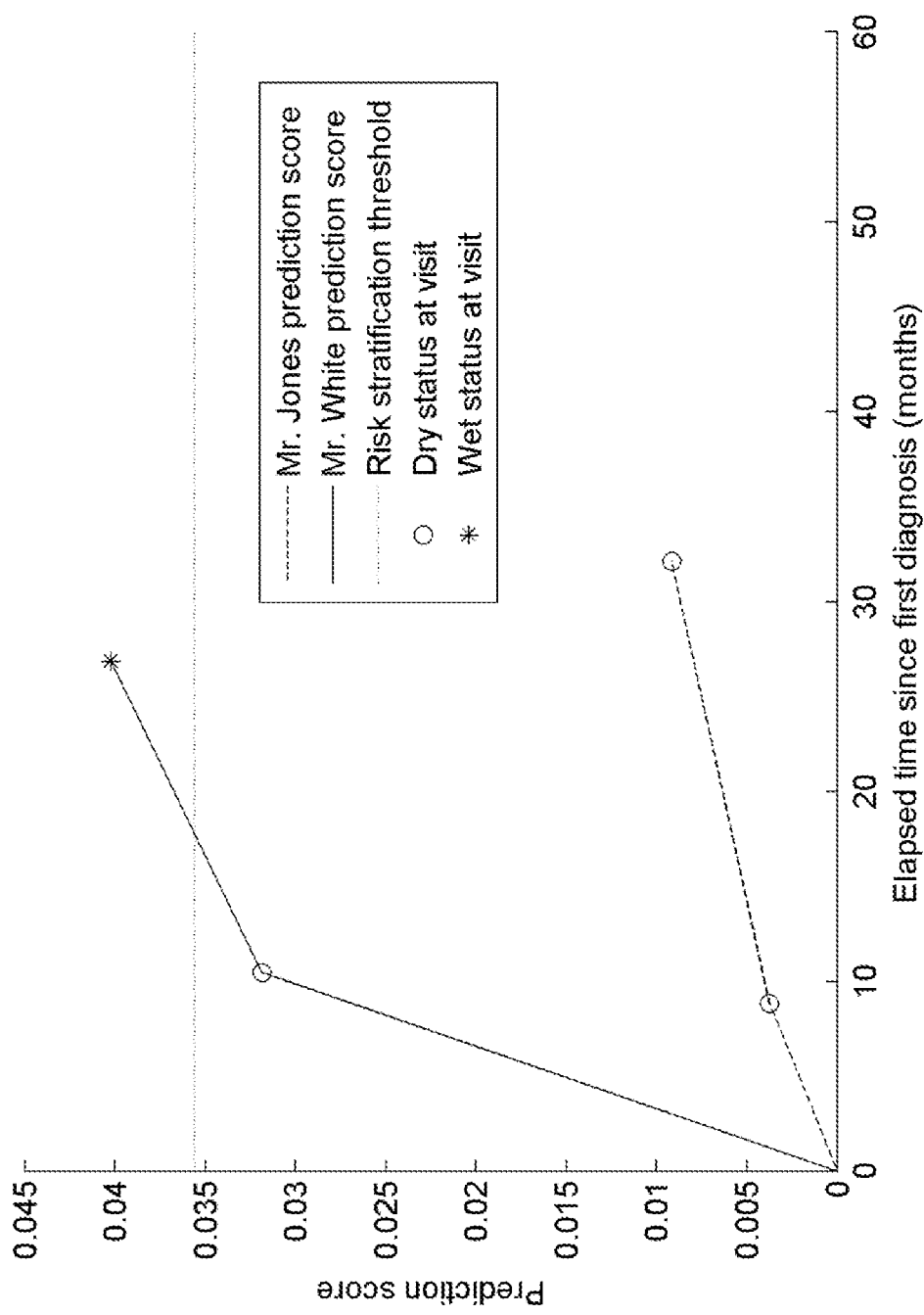
FIG. 11 is an example representation of prediction scores computed for two eyes of two different patients as they make several clinic visits. The prediction scores for the two patients are displayed as a function of time elapsed since each patient clinical visit. The computed scores are updated as each patient makes a new visit to the clinic. The horizontal line indicates the threshold score for risk stratification. The observations where a progression event was later verified are displayed with a star, while those where no progression event was later detected are displayed with a circle.

These examples are based on data collected from two actual eyes of two patients during clinical practice, as shown in FIG. 11.

Subject 1 ("Mr. Jones") makes a first visit to the clinic and is diagnosed with dry AMD in his right eye. The quantitative imaging features are extracted by the present method, with values: F1=665.96, F2=0, F12=0.0469, F15=0.0856, F19=0. As stated above, F1 is the age of the patient in months; F12 is the maximum height of drusen measured in SD-OCT at clinical visit (in mm); F15 is the (standard deviation of pixel intensity (reflectivity) inside drusen regions, measured from normalized SD-OCT cube at clinical visit (cube normalized to take values from 0 to 1), and F19 is Slope of linear fit through time of F2 (gender of patient) considering all patient SD-OCT imaging history (in mm$^2$/(drusen months))

The computed risk score using the present method at time t=8.83 months is S(t)=0.0037. Since this score is lower than T=0.0356, the eye is classified as low risk. A future visit at this later time revealed that this eye did not progress, and the prediction was correct.

Subject 1 ("Jones") makes to the clinic another visit 8.83 months after his first visit. A new set of quantitative imaging features are extracted by the invention, with values: F1=674.79, F2=0, F12=0, F15=0, F19=0.0203. The computed risk score from the present method at time t=23.3 months is S(t)=0.0092. Since this score is lower than T=0.0356, the patient is classified as low risk. A future visit at this later time revealed that this eye did not progress, and the prediction was correct.

Subject 2 ("Mr. White") makes a first visit to the clinic and is diagnosed with dry AMD in his left eye. The quantitative imaging features are extracted by the present method, with values: F1=1048.2, F2=0, F12=0.1055, F15=0.0986, F19=0. The computed risk score produced by the present method at time t=10.47 is S(t)=0.0319. Since this score is lower than T=0.0356, the patient is classified as low risk. A future visit at this later time revealed that this eye did not progress, and the prediction was correct.

At a visit subject 2 makes to the clinic 10.47 months after his first visit, a new set of quantitative imaging features is extracted by the present method, with values: F1=1058.6, F2=0, F12=0.0508, F15=0.0881, F19=-0.0043. The computed risk score produced by the present method at time t=18.033 is S(t)=0.0402. Since this score is higher than T=0.0356, the eye is classified as high risk. A future visit at this later time revealed that this eye progressed, and the prediction was correct.

Instrumentation

As noted above, the data included in the present evaluations were collected using a commercially available OCT device, a Carl Zeiss CirrusOCT. This device is currently a state-of the-art imaging device that provides direct cross-sectional images of the retina. This device comes with algorithms for analyzing OCT scans. Such instrumentation can be programmed or controlled by a separate computer to carry out most, or all, of the above-described steps. In particular, the SD-OCT device according to the present invention is programmed to segment the retina into multiple layers as shown, for example, in FIGS. 2B and 2C. Drusen are segmented according to the process as described, for example, in connection with FIG. 3 and refined as described, e.g., in connection with FIG. 4. En face measurements are also carried out as shown, for example, in FIGS. 6A and 6D. These data are manipulated by programmed instructions to carry out the described calculations and to output a risk score. The device also contains media for storing available patient knowledge, including previous SD-OCT scans of a given patient and other patients; demographics such as age, gender and medical history, the existence of AMD or other eye diseases, etc. The instrument can be programmed to carry out automated RPE inner and outer calculations and drusen segmentation, based on the above-described boundary determinations. It can also calculate the above-described parameters $F_5$-$F_{26}$. Furthermore, various computerized SD-OCT devices can be programmed to apply these factors to the above-described β (correction) factors to produce a score that is calculated as described in sections (4) and (5) above.

REFERENCES

1. Klein, R., Klein, B., Jensen, S., Meuer, S., "The five-year incidence and progression of age-related maculopathy: the Beaver Dam Eye Study", Ophthalmology. 104 (1), 7-21, 1997.
2. Wong, R. W., Richa, D. C., Hahn, P., Green, W. R., Dunaief, J. L., "Iron toxicity as a potential factor in AMD", Retina, 27 (8):997-1003 (PMID 18040235), 2007.
3. Age-Related Eye Disease Study Research Group, "A Randomized, Placebo-Controlled, Clinical Trial of High-Dose Supplementation with Vitamins C, and E, Beta Carotone, and Zinc for Age-Related Macular Degeneration and Vision Loss: AREDS Report No. 8", Arch. Opththalmol., 119 (10): 1417-1436, 2001.
4. Age-Related Eye Disease Study Research Group, "A Simplified Severity Scale for Age-Related Macular Degeneration: AREDS Report No. 18", Arch. Ophthalmol., 123 (11): 1570-1574, 2005.
5. Feigl, B., Morris, C. P., "The challenge of predicting macular degeneration", Current Medical Research and Opinion, 27 (9): 1745-1748, 2011.
6. Hageman, G. S., Anderson, D. H., Johnson, L. V., et al., "A common haplotype in the complement regulatory gene factor H (HF1/CFH) predisposes individuals to age-related macular degeneration", PNAS 102 (20): 7227-7232, 2005.
7. Hughes, A. E., Orr, N., Esfandiary, H., Diaz-Tones, M., Goodship, T., Chakravarthy, U., "A common CFH haplotype, with deletion of CFHR1 and CFHR3, is associated with lower risk of age-related macular degeneration", Nature Genetics 38 (10): 1173-1177, 2006.
8. Seddon, J. M., Francis, P. J., George, S., Schultz, D. W., Rosner, B., Klein, M. L., "Association of CFH Y402H and LOC387715 A69S with progression of age-related macular degeneration", JAMA 297 (16): 1793-1800, 2007.
9. Hageman, G. S., Gehrs, K., Lejnine, S., et al., "Clinical validation of a genetic model to estimate the risk of developing choroidal neovascular age-related macular degeneration", Human Genomics 5 (5):420-440, 2011.
10. Yu, Y., Reynolds, R., Rosner, B., Daly, M. J., Seddon, J. M., "Prospective assessment of genetic effects on progression to different stages of age-related macular degeneration", IOVS 53 (3): 1548-1556, 2012.
11. Seddon, J. M., Reynolds, R., Maller, J., Fagerness, J. A., Daly, M. J., Rosner, B., "Prediction model for prevalence and incidence of advanced age-related macular degeneration based on genetic, demographic, and environmental variables", IOVS 50 (5), 2009.
12. Seddon, J. M., Reynolds, R., Yu, Y., Rosner, B., "Validation of a prediction algorithm for progression to advanced macular degeneration subtypes", JAMA Ophthalmol. 131 (4): 448-455, 2013.
13. Perlee, L. T., Bansal, A. T., Gehrs, K., et al., "Inclusion of genotype with fundus phenotype improves accuracy of predicting choroidal neovascularization and geographic atrophy", Ophthalmol., in press, 2013.
14. Abdelsalam, A., Del Priore, L., Zarbin, M. A., "Drusen in age-related macular degeneration: pathogenesis, natural course, and laser photocoagulation-induced regression", Surv. Ophthalmol. 44, 1-29, 1999.
15. Friberg, T. R., Bilonick, R, A, Brennen, P. M., "Analysis of the relationship between drusen size and drusen area in eyes with age-related macular degeneration", Ophthalmic Surg Lasers Imaging 42 (5):369-75 (PMID 21899243), 2011.
16. Smith, R. T., Sohrab, M. A., Pumariega N. M., Mathur, K., Haans, R., Blonska, A., Uy, K., Despriet, D., Klaver, C., "Drusen analysis in a human-machine synergistic framework", Arch. Ophthalmol. 129 (1):40-7 (PMID21220627), 2011.
17. Friberg, T. R., Bilonick, R. A., Brennen, P., "Is drusen area really so important? An assessment of risk of conversion to neovascular AMD based on computerized measurements of drusen", Invest Ophthalmol Vis Sci. 53(4):1742-51 (PMID 22395875), 2012.
18. Huang, D., Swanson, E. A., Lin, C. P., Schuman, J. S., Stinson, W. G., Chang, W., Hee, M. R., Flotte, T., Gregory, K., Puliafito, C. A., Fujimoto, J. G., "Optical coherence tomography", Science 254: 1178-81, 1991.
19. Zysk, A. M., Nguyen, F. T., Oldenburg, A. L., Marks, D. L., Boppart, S. A., "Optical coherence tomography: a review of clinical development from bench to bedside", Journal of Biomed. Optics 12 (5): 2007.
20. Alexander, L., and Choate, W., "Optical coherence tomography: rewriting the standard of care in diagnosis, management and interventional assessment", Rev. optometry 141 (9): 10E-CE, 2004.
21. Jain, N., Farsiu, S., Khanifar, A. A., Bearelly, S., Smith, R. T., Izatt, J. A., Toth, C. A., "Quantitative comparison of drusen segmented on SD-OCT versus drusen delineated on color fundus photographs", Invest. Ophthalmol. Vis. Sci., 51 (10):4875-83 (PMID 20393117), 2010.
22. Schuman, S. G., Koreishi, A. F., Farsiu, S., Jung, S. H., Izatt, J. A., Toth, C. A., "Photoreceptor layer thinning over drusen in eyes with agre-related macular degeneration imaged in vivo with spectral-domain optical coherence tomography", Ophthalmology 116 (3): 488-496, 2009.
23. Khanifar, A. A., Koreishi, A. F., Izatt, J. A., Toth, C. A., "Drusen ultrastructure imaging with Spectral domain Optical coherence Tomography in Age-related Macular Degeneration", Ophthalmology 115 (11):1883-90, 2008.
24. Yi. K., Mujat. M., Park. B. H., Sun. W., Miller. J. W., Seddon. J. M., Young. L. H., de Boer. J. F., Chen, T. C., "Spectral domain optical coherence tomography for quantitative evaluation of drusen and associated structural changes in non-neovascular age-related macular degeneration", Br. J. Ophthalmol. 93 (2):176-81 (PMID 18697811), 2009.
25. Chiu, S. J., Izatt, J. A., O'Connell, R. V., Winter, K. P., Toth, C. A., Farsiu, S. "Validated automatic segmentation of AMD pathology including drusen and geographic atrophy in SD-OCT images", Invest. Ophthalmol. Vis. Sci. 53(1):53-61 (PMID 22039246), 2012.
26. Nelder, J. A., Wedderburn, R. W. M., "Generalized Linear Models", Journal of the Royal Statistical Society Series A (General), 135 (3):370-84, 1972.
27. Tibshirani, R., "Regression Shrinkage and Selection Via the Lasso", Journal of the Royal Statistical Society, Series B, 58:267-88, 1994.
28. Cox, D. R., "Regression models and life tables (with discussion)", Journal of the Royal Statistical Society, Series B 34:187-220, 1972.
29. Chen, Q., Leng, T., Zheng, L., Kutzscher, L., Ma, J., de Sisternes, L., Rubin, D. L., "Automated drusen segmentation and quantification in SD-OCT images", Medical Image Analysis, 17:1058-1072 2 Jul. 2013.
30. Fitzmaurice, G. M., Laird, N. M., Ware, J. H., "Applied Longitudinal Analysis". John Wiley & Sons, Inc., ISBN: 978-0-470-38027-7: 326-328, 2004.

31. Storey, J. D. "A direct approach to false discovery rates". Journal of the Royal Statistical Society 64 (3): 479-498, 2002.
32. Storey, J. D., and Tibshirani, R., "Statistical significance for genomewide studies". Proc. Nat. Acad. Sci. 100 (16): 9440-9445, 2003.
33. Kaplan, E. L., Meier, P., "Nonparametric estimation from incomplete observations." J. Amer. Statist. Assn. 53:457-481, 1958.
34. Greenwood, M. Jr., "The Natural Duration of Cancer", Reports of Public Health and Related Subjects 33: 1-26, 1926.

CONCLUSION

The above specific description is meant to exemplify and illustrate the method of the invention and should not be seen as limiting the scope of the invention, which is defined by the literal and equivalent scope of the appended claims Any patents or publications mentioned in this specification are indicative of levels of those skilled in the art to which the patent or publication pertains as of its date and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material to which is referred.

What is claimed is:

1. A method for analyzing optical coherence tomography (OCT) images of a retina, comprising the steps of:
    (a) obtaining an OCT image of a subject's retina and corresponding demographic data, including age, gender, and presence of age-related macular degeneration (AMD) in the subject;
    (b) processing the OCT image of step (a) to define an inner retinal pigment epithelium boundary and an outer retinal pigment epithelium boundary;
    (c) identifying drusen using the boundaries defined in step (b);
    (d) characterizing identified drusen by quantitative values representing characteristics of identified drusen; and
    (e) using the quantitative values obtained in step (d) and demographic data from step (a) to obtain a score indicating a likelihood of progressing from dry AMD to wet AMD.

2. The method of claim 1 wherein the step of characterizing identified drusen comprises determining values for one or more of:
    (i) drusen slope expressed as height versus en face area; (ii) drusen reflectivity expressed as pixel intensity; (iii) drusen height; (iv) drusen area, (v) drusen volume, and (vi) drusen number.

3. The method of claim 2 further comprising a step wherein values (i) through (vi) are measured at separate time points, and a difference in measurements between time points is calculated.

4. The method of claim 1 wherein the quantitative values include one, two or three of maximum height of drusen and standard deviation of pixel intensity in a normalized spectral domain optical coherence tomography (SD-OCT) image inside drusen regions; and a slope of linear fit through time of mean en face area per drusen.

5. The method of claim 1 wherein the quantitative values are a measurement of standard deviation of drusen reflectivity and changes with time in mean drusen area.

6. The method of claim 1 comprising using SD-OCT to generate the OCT images.

7. The method of claim 1 wherein said demographic data of step (a) further includes at least one, two or three of: (a) exceeding an age of 60 years; (b) a previous diagnosis of dry AMD; and (c) a genetic predisposition to AMD.

8. The method of claim 1 wherein the step of processing an OCT image in step (b) further includes determination of one or more of the following retina layer boundaries: inner limiting membrane (ILM), inner retinal nerve fiber layer boundary (iRNFL), outer retinal nerve fiber layer boundary (oRNFL), outer boundary of the inner plexiform layer (IPL), outer boundary of the inner nuclear layer (INL), outer boundary of the outer plexiform layer (OPL), inner boundary of the inner segment/outer segment junction (IS), and outer boundary of the inner segment/outer segment junction (OS), in addition to inner retinal pigment epithelium boundary (iRPE), and outer retinal pigment epithelium boundary (oRPE).

9. The method of claim 8 comprising determining at least nine boundary layers.

10. The method of claim 8 wherein boundary determination includes calculation of particular curvature of boundary layers.

11. The method of claim 1 wherein the step of characterizing identified drusen further comprises the step of measuring maximum drusen height, wherein an increase in drusen height indicates an increased likelihood of progression to wet AMD.

12. The method of claim 1 wherein the step of characterizing identified drusen further comprises measuring standard deviation of pixel intensity resulting from drusen reflectivity.

13. The method of claim 1 further comprising the step of comparing previously measured values from other patients to those measured in step (d), wherein increased values in measured values in step (d) compared to previously measured values indicate an increased likelihood of progression from dry AMD to wet AMD.

14. A method for analyzing optical coherence tomography (OCT) images of a retina, comprising the steps of:
    (a) obtaining a subject's demographic data, including age, gender, presence of age-related macular degeneration ("AMD"), and further obtaining OCT images of the subject's retina;
    (b) processing the OCT images of step (a) to define segmentations of three dimensional retinal layers, including an inner boundary and an outer boundary of retinal pigment epithelium (RPE);
    (c) identifying drusen segmentations using boundaries obtained in step (b);
    (d) using drusen segmentations calculated in step (c) to determine a plurality of three-dimensional drusen features having individual numerical values; and
    (e) using (i) the individual numerical values obtained in step (d); (ii) historical numerical values corresponding to values measured in step (d); and (iii) subject demographic data in step (a) to obtain an AMD score representing a likelihood of progression of AMD.

15. A method for assessing risk for progression from Age-Related Macular Degeneration (AMD), comprising the steps of:
    (a) obtaining subject demographic data and OCT images of said retina;

(b) processing said OCT images to define segmentations of three dimensional retinal layers, including an inner boundary and an outer boundary of retinal pigment epithelium (RPE);
(c) identifying drusen segmentations using boundaries obtained in step (b);
(d) using drusen segmentations identified in step (c) to determine a plurality of three dimensional drusen features having individual numerical values comprising
   (i) number of drusen identified,
   (ii) extent of retinal area affected by drusen,
   (iii) mean area per drusen detected,
   (iv) mean volume of drusen detected,
   (v) shape of drusen detected,
   (vi) density of drusen, and
   (vii) reflectivity of drusen; and
(e) using (i) the individual numerical values obtained in step (d); (ii) historical numerical values corresponding to values measured in step (d); and (iii) subject demographic data in step (a) to assess a risk of progression of AMD, wherein higher values of values in (i) through (vii) indicate a higher risk of progression.

16. An OCT device comprising
(a) storage means for holding a subject's demographic data, including age, gender, and presence of age-related macular degeneration (AMD);
(b) components for obtaining OCT images of the subject's retina;
(c) instructions for analyzing OCT images of the subject to define an inner retinal pigment epithelium boundary and an outer retinal pigment epithelium boundary;
(d) instructions for identifying drusen using boundaries to identify drusen by quantitative values for at least one of: (i) drusen slope expressed as height versus en face area; (ii) drusen reflectivity expressed as pixel intensity; a value that is at least one of (iii) drusen height; (iv) drusen area, (v) drusen volume, (vi) drusen number and (vii) drusen reflectivity,
wherein measured values (i) through (vii) as determined in step (d) are measured at separate time points, and a difference in measurements between time points is calculated; and
(e) logic means for using quantitative values obtained in step (d) and demographic data from step (a) to obtain a score wherein increases in value in the quantitative values indicates an increased likelihood of progressing from dry AMD to wet AMD.

17. The OCT device of claim 16 wherein the quantitative values used in step (e) are all of (iii) through (vii), inclusive.

18. The OCT device of claim 16 further comprising an SD-OCT device.

19. An OCT device configured to carry out and store retinal images derived according to instructions, comprising:
(a) obtaining an OCT image of a subject's retina and corresponding demographic data, including age, gender, and presence of age-related macular degeneration (AMD) in the subject;
(b) processing the OCT image of step (a) to define an inner retinal pigment epithelium boundary and an outer retinal pigment epithelium boundary;
(c) identifying drusen using the boundaries defined in step (b);
(d) characterizing identified drusen by quantitative values representing characteristics of identified drusen; and
(e) using quantitative values obtained in step (d) and demographic data from step (a) to obtain a score, wherein a score over a threshold indicates an increased likelihood of progressing from dry AMD to wet AMD.

* * * * *